US009886549B2

(12) United States Patent
Buck et al.

(10) Patent No.: US 9,886,549 B2
(45) Date of Patent: Feb. 6, 2018

(54) METHOD AND SYSTEM FOR SETTING TIME BLOCKS

(75) Inventors: Schuyler Buck, Muncie, IN (US); Morris J. Young, Indianapolis, IN (US); Jason Bush, Fishers, IN (US); Christopher Richard Baker, Fishers, IN (US); Scott W. Leahy, Fort Wayne, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 2090 days.

(21) Appl. No.: 11/999,968

(22) Filed: Dec. 7, 2007

(65) Prior Publication Data

US 2009/0150177 A1 Jun. 11, 2009

(51) Int. Cl.
*G06F 19/00* (2011.01)
*G06Q 50/22* (2012.01)

(52) U.S. Cl.
CPC ......... *G06F 19/3406* (2013.01); *G06Q 50/22* (2013.01)

(58) Field of Classification Search
CPC G06Q 10/109; G06F 19/3406; Y10S 715/963
USPC ....................................................... 705/2–3
See application file for complete search history.

(56) References Cited

U.S. PATENT DOCUMENTS

| 5,251,126 A | 10/1993 | Kahn et al. |
| 5,634,100 A * | 5/1997 | Capps ................ G06F 15/0266 705/7.12 |
| 5,671,409 A | 9/1997 | Fatseas et al. |
| 5,893,073 A * | 4/1999 | Kasso ................ G06F 17/2205 705/7.12 |
| 6,024,699 A | 2/2000 | Surwit et al. |
| 6,032,119 A | 2/2000 | Brown et al. |
| 6,322,502 B1 | 11/2001 | Schoenberg et al. |
| 6,356,256 B1 | 3/2002 | Leftwich |
| 6,425,863 B1 | 7/2002 | Werner et al. |
| 6,562,001 B2 | 5/2003 | Lebel et al. |
| 6,564,105 B2 | 5/2003 | Starkweather et al. |
| 6,571,128 B2 | 5/2003 | Lebel et al. |
| 6,577,899 B2 | 6/2003 | Lebel et al. |
| 6,585,644 B2 | 7/2003 | Lebel et al. |
| 6,593,942 B1 * | 7/2003 | Bushmitch ................ G06F 1/14 715/721 |
| 6,605,038 B1 | 8/2003 | Teller et al. |
| 6,635,014 B2 | 10/2003 | Starkweather et al. |
| 6,648,821 B2 | 11/2003 | Lebel et al. |

(Continued)

FOREIGN PATENT DOCUMENTS

| EP | 0 970 655 A1 | 1/2000 |
| EP | 0 649 316 B1 | 12/2000 |

(Continued)

OTHER PUBLICATIONS

Shahar, Y. et al., "*Distributed, intelligent, interactive visualization and exploration of time-oriented clinical data and their abstractions*"; Artificial Intelligence in Medicine, 2006, pp. 115-135, vol. 38.

(Continued)

*Primary Examiner* — Joy Chng
(74) *Attorney, Agent, or Firm* — Harness Dickey

(57) ABSTRACT

A method and system for setting time blocks of a repeating time period is disclosed. The method and system may be a part of a healthcare management software system.

27 Claims, 21 Drawing Sheets

(56) References Cited

U.S. PATENT DOCUMENTS

| | | | |
|---|---|---|---|
| 6,659,948 | B2 | 12/2003 | Lebel et al. |
| 6,668,196 | B1 | 12/2003 | Villegas et al. |
| 6,687,546 | B2 | 2/2004 | Lebel et al. |
| 6,694,191 | B2 | 2/2004 | Starkweather et al. |
| 6,733,446 | B2 | 5/2004 | Lebel et al. |
| 6,740,075 | B2 | 5/2004 | Lebel et al. |
| 6,758,810 | B2 | 7/2004 | Lebel et al. |
| 6,781,522 | B2 | 8/2004 | Sleva et al. |
| 6,804,656 | B1 | 10/2004 | Rosenfeld et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,852,104 | B2 | 2/2005 | Blomquist |
| 6,873,268 | B2 | 3/2005 | Lebel et al. |
| 6,958,705 | B2 | 10/2005 | Lebel et al. |
| 7,020,508 | B2 | 3/2006 | Stivoric et al. |
| 7,024,236 | B2 | 4/2006 | Ford et al. |
| 7,029,455 | B2 | 4/2006 | Flaherty |
| 7,041,468 | B2 | 5/2006 | Drucker et al. |
| 7,050,735 | B2 | 5/2006 | Bardolatzy et al. |
| 7,063,665 | B2 | 6/2006 | Hasegawa et al. |
| 7,082,334 | B2 | 7/2006 | Boute et al. |
| 7,165,062 | B2 | 1/2007 | O'Rourke |
| 7,179,226 | B2 | 2/2007 | Crothall et al. |
| 7,207,009 | B1 | 4/2007 | Aamodt et al. |
| 7,992,102 | B1 * | 8/2011 | De Angelo ............ G06F 3/0482 715/804 |
| 2002/0016568 | A1 | 2/2002 | Lebel et al. |
| 2002/0029776 | A1 | 3/2002 | Blomquist |
| 2002/0040208 | A1 | 4/2002 | Flaherty et al. |
| 2002/0140976 | A1 | 10/2002 | Borg et al. |
| 2002/0193679 | A1 | 12/2002 | Malave et al. |
| 2003/0011646 | A1 | 1/2003 | Levine et al. |
| 2003/0065308 | A1 | 4/2003 | Lebel et al. |
| 2003/0065536 | A1 | 4/2003 | Hansen et al. |
| 2003/0098869 | A1 | 5/2003 | Arnold et al. |
| 2003/0145206 | A1 | 7/2003 | Wolosewicz et al. |
| 2003/0163088 | A1 | 8/2003 | Blomquist |
| 2003/0199739 | A1 | 10/2003 | Gordon et al. |
| 2003/0208113 | A1 * | 11/2003 | Mault ............... A61B 5/14532 600/316 |
| 2004/0073464 | A1 | 4/2004 | Huang |
| 2004/0117210 | A1 * | 6/2004 | Brown ................ A61B 5/087 705/2 |
| 2004/0119742 | A1 | 6/2004 | Silbey et al. |
| 2004/0172284 | A1 | 9/2004 | Sullivan et al. |
| 2005/0004947 | A1 | 1/2005 | Emlet et al. |
| 2005/0052458 | A1 * | 3/2005 | Lambert ............... G06F 3/0481 345/440 |
| 2005/0137653 | A1 | 6/2005 | Friedman et al. |
| 2005/0159977 | A1 | 7/2005 | Green et al. |
| 2005/0192844 | A1 | 9/2005 | Esler et al. |
| 2006/0010014 | A1 | 1/2006 | Brown |
| 2006/0010098 | A1 | 1/2006 | Goodnow et al. |
| 2006/0020491 | A1 | 1/2006 | Mongeon et al. |
| 2006/0031094 | A1 | 2/2006 | Cohen et al. |
| 2006/0272652 | A1 | 12/2006 | Stocker et al. |
| 2007/0033074 | A1 | 2/2007 | Nitzan et al. |
| 2007/0048691 | A1 | 3/2007 | Brown |
| 2007/0055940 | A1 | 3/2007 | Moore et al. |
| 2007/0089071 | A1 | 4/2007 | Zinn et al. |
| 2007/0179352 | A1 | 8/2007 | Randlov et al. |
| 2007/0189590 | A1 | 8/2007 | Fidrich et al. |
| 2007/0232866 | A1 | 10/2007 | Nephin et al. |
| 2007/0276197 | A1 | 11/2007 | Harmon |
| 2008/0319294 | A1 * | 12/2008 | Taub ................. A61B 5/14532 600/365 |

FOREIGN PATENT DOCUMENTS

| | | |
|---|---|---|
| EP | 1 179 769 | 2/2002 |
| EP | 1 194 864 A2 | 4/2002 |
| EP | 1 839 615 | 10/2007 |
| JP | 2004145774 A | 5/2004 |
| JP | 2004145775 A | 5/2004 |
| JP | 2004145776 A | 5/2004 |
| JP | 2007058685 A | 3/2007 |
| WO | WO00018449 | 4/2000 |
| WO | WO00072181 | 11/2000 |
| WO | WO02000111 | 11/2000 |
| WO | WO02078512 | 10/2002 |
| WO | WO03015838 | 2/2003 |
| WO | WO05037095 | 4/2005 |
| WO | WO05096206 | 10/2005 |
| WO | WO06050485 | 2/2006 |
| WO | WO07093482 | 8/2007 |

OTHER PUBLICATIONS

"CoPilot Health Management System Version 3.1," User's Guide, Mar. 2007, 230 pp., ART 10641 Rev. D, Abbott Diabetes Care, Inc.

"MediSense® Precision Link® Diabetes Data Management Software," User's Guide, May 2006, 58 pp., 116-412 Rev. AC, Abbott Diabetes Care, Inc.

Albisser, Michael A.; "A Graphical User Interface for Diabetes Management Than Integrates Glucose Prediction and Decision Support," Diabetes Technology & Therapeutics, 2005, pp. 264-273, vol. 7, No. 2.

Janssen et al., "Acensia® Winglucofacts® Professional Intelligent Diabetes Management Software is an Effective Tool for the Management of Diabetes," Bayer HealthCare Clinical Summary Report, Jul. 2005, 10 pp.

Joshy et al.; "Diabetes Information Systems: A Rapidly Emerging Support for Diabetes Surveillance and Care," Diabetes Technology & Therapeutics, 2006, pp. 587-597, vol. 8, No. 5.

"OneTouch Diabetes Management Software," User Manual, 2006, 173 pp., v. 2.3.1, Lifescan, Inc.

"Getting Started, CareLink Personal Therapy Management Software for Diabetes," Brochure, 2007, 20 pp., Medtronic Minimed, Inc.

"Accu-Chek® Camit Pro Diabetes Management Software," User's Manual, 2005, 220 pp., v.2.1 and Addendum 2.4, Roche Diagnostics Corp.

"Accu-Chek® Compass Diabetes Care Software," User's Guide, 2005, 74 pp., Roche Diagnostics Corp.

"Accu-Chek® Diabetes Assistant," accessed with notional data and printed from www.diabetesassistant.com on Jan. 16, 2007, 20 pp., Roche Diagnostics Corp.

* cited by examiner

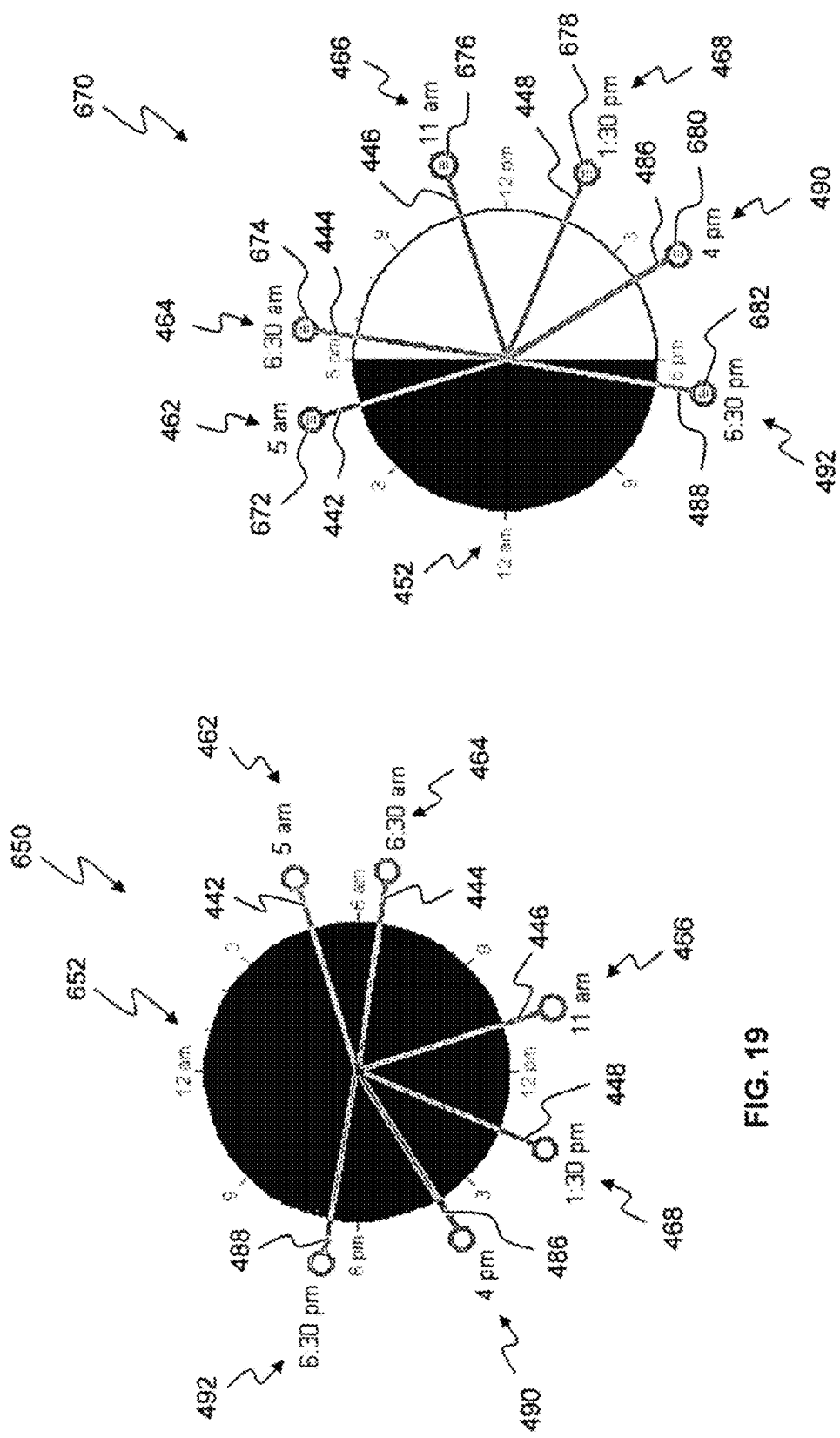

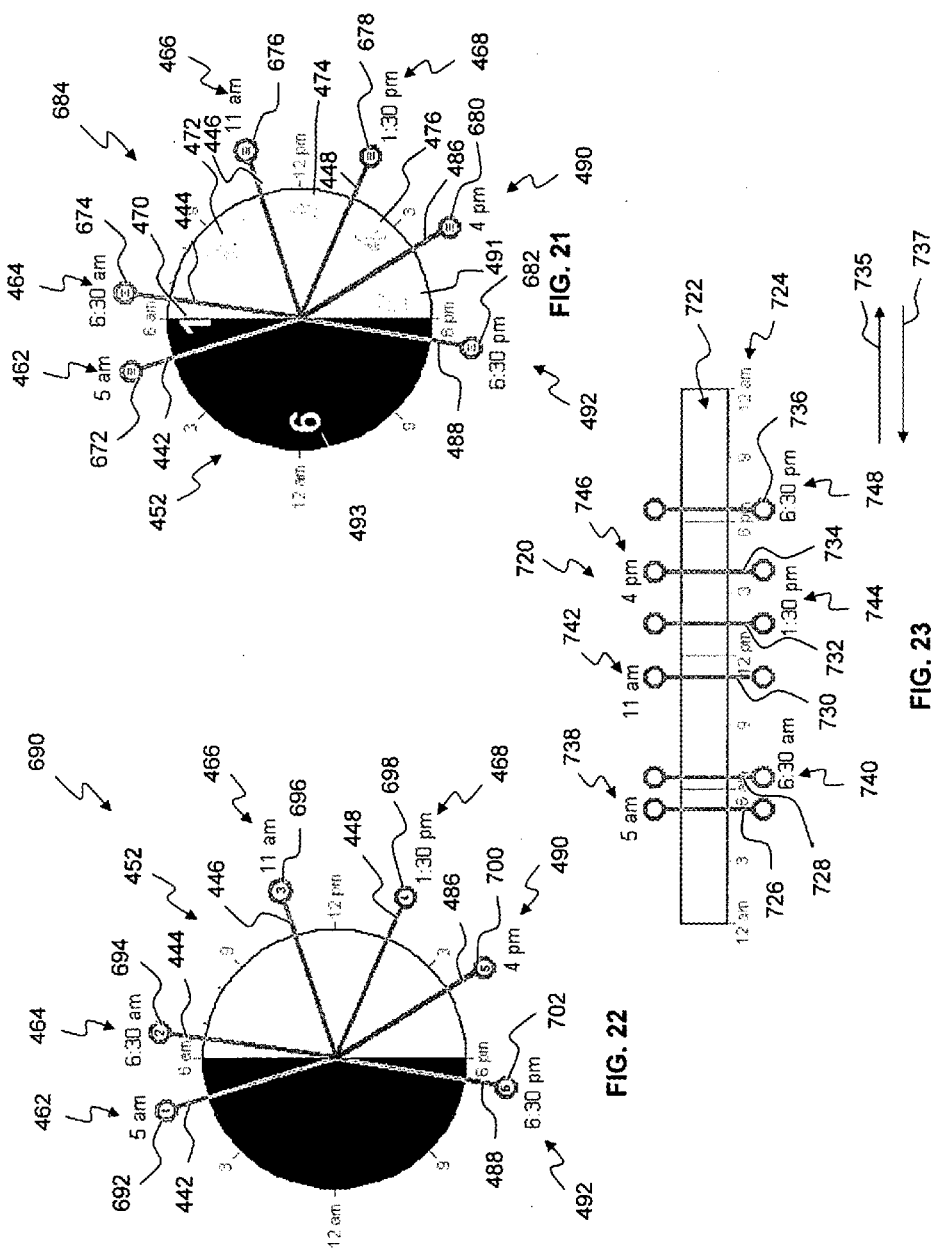

METHOD AND SYSTEM FOR SETTING TIME BLOCKS

FIELD OF THE INVENTION

The invention relates a method and system for setting sub-divisions of a repeating periodic parameter and in particular to a method and system for setting time blocks of a repeating time period in a healthcare management software system.

BACKGROUND OF THE INVENTION

Many fields of medical treatment and healthcare require monitoring of certain body functions, physical states and conditions, and patient behaviors. Thus, e.g., for patients suffering from diabetes, a regular check of the blood glucose level forms an important part of the daily routine. The blood glucose level has to be determined quickly and reliably, often several times per day. Medical devices are used to facilitate the collection of medical information without unduly disturbing the lifestyle of the patient. A large number of medical devices for monitoring various body functions are commercially available. Also, medical treatment and healthcare may require monitoring of exercise, diet, meal times, stress, work schedules and other activities and behaviors.

To reduce the frequency of necessary visits to doctors, the idea of home care gained popularity over the recent years. Technological advancements in medicine led to the increased use of medical devices. Many of these medical devices, such as meters and medicine delivery devices, are able to collect and store measurements and other data for long periods of time. Other devices, such as computers, portable digital assistants (PDAs), and cell phones, have been adapted to medical uses by the development of software directed to the collection of healthcare data. These advancements led to the development of health management systems that enable collection and use of large numbers of variables and large amounts of healthcare data.

A common feature of health management systems is the ability to convey information. Information can include raw data, graphical representations of data such as statistical display objects, explanations and textual interpretations, inferential information and so on. Communication and understanding can be improved by using interactive graphs to convey information. Interactivity is achieved using computing devices and software applications. Generally described, individuals can interact with software applications residing on computing devices, such as personal computers, hand-held computers, mobile computing devices, and the like in a variety of ways. In one particular embodiment, the development of graphical user interfaces facilitate user interaction with these various software applications resident in or accessible by the computing device. For example, a user may manipulate a graphical user interface to interact with a data processing application or to communicate with other computing devices and/or users via a communication network.

In a typical embodiment, a graphical user interface may display a number of display objects that are individually manipulable by a user utilizing a user input device. For example, the user can utilize a computer keyboard, mouse, touch screen, touch pad, roller ball or voice commands and the like to select a particular display object and to further initiate an action corresponding to the selected display object. While user input devices have been described in the context of devices configured to manipulate display objects and provide commands to the computing device, generally speaking a user input device is any device capable of providing user input to a computing device and input is not limited to the provision of commands. User input may additionally comprise data which may be provided by medical devices, or computing devices including PDAs and phones.

In the area of diabetes care, several software packages are available for use with a glucose meter or insulin pump. These software packages divide a day up in a number of discrete time blocks. Exemplary time blocks include Pre-Breakfast, Post-Breakfast, Pre-Lunch, Post-Lunch, Pre-Dinner, Post-Dinner, and Night. Some of these software packages permit the altering of an endpoint of the time blocks. Further, some of these software packages permit the altering of an endpoint of the time blocks independently for working days and non-working days.

SUMMARY OF THE INVENTION

The present invention relates generally to software systems, such as a healthcare management software system, and in particular to setting sub-divisions of a periodic parameter, such as time blocks for a repeating time period for a healthcare management software system. A healthcare management software system is provided. The healthcare management software system includes the ability to review physiological information about one or more patients.

In an exemplary embodiment of the present disclosure, a method of characterizing time for physiological information within a healthcare management software system is provided. The method including the steps of receiving a number selection of a plurality of time blocks for a repeating time period; and receiving one or more duration selections related to a duration for at least one of the time blocks. In one example, the number of time blocks is at least two and up to twelve. In another example, the one or more duration selections are based on a selected position of one or more time block dividers provided on a user interface of a computing device. In one variation thereof, the time block dividers are positioned relative to a linear representation of the repeating time period. In another variation thereof, the time block dividers are positioned relative to a clock representation of the repeating time period, the time block dividers being spokes emanating from a center of the clock representation of the repeating time period. In a further example, the method further includes the steps of receiving a plurality of blood glucose values and corresponding test times; graphically presenting the plurality of blood glucose values based on the time block including the corresponding test time. In a variation thereof, the step of graphically presenting the plurality of blood glucose values based on the time block including the corresponding test time includes the steps of: graphically representing the plurality of time blocks; graphically representing the plurality of blood glucose values; and graphically representing a plurality of classifications for the plurality of blood glucose values. In another variation thereof, the plurality of blood glucose values and corresponding test times are provided by a blood glucose meter. In yet another variation thereof, the plurality of blood glucose values and corresponding test times are provided by an infusion pump. In yet a further example, the method further includes the steps of receiving a first type selection for a first instance of the repeating time period; and receiving a second type selection for a second instance of the repeating time period.

In another embodiment of the present disclosure, a user interface of a healthcare management software system for a computing device having access to a display and a user input device is provided. The user interface including a number selection input to define a number of time blocks of a repeating time period; and a plurality of duration selection inputs which determine for each time block a portion of the repeating time period to which the respective time block corresponds. In one example, the plurality of duration selection inputs are time block dividers which are positionable with the user input device relative to a linear representation of the repeating time period. In a variation thereof, a first time block divider separates a first time block and a second time block. A duration of the first time block and a duration of the second time block both being altered by a position of the first time block divider relative to the linear representation of the repeating time period. In another example, the plurality of duration selection inputs are time block dividers which are positionable with the user input device relative to a clock representation of the repeating time period. The time block dividers being spokes emanating from a center of the clock representation of the repeating time period. In a variation thereof, a first time block divider separates a first time block and a second time block. A duration of the first time block and a duration of the second time block both being altered by a rotational position of the first time block divider relative to the clock representation of the repeating time period. In yet another example, each time block a textual label. In one variation thereof, a label text for at least one textual label is user-specified.

In a further exemplary embodiment of the present disclosure, a method of characterizing time for physiological information within a healthcare management software system is provided. The method including the steps of selecting a number of a plurality of time blocks for a plurality of repeating time periods; and classifying each repeating time period as one of a plurality of types of repeating time periods. In one example, the plurality of repeating time periods are days and a first type of repeating time period is a work day and a second type of repeating time period is a non-work day. In a variation thereof, the method further includes receiving one or more duration selections related to a duration for at least one of the time blocks.

In yet another exemplary embodiment of the present disclosure, a user interface of a computing device having access to a display and a user input device is provided. The user interface including a number selection input to define a number of time blocks of a repeating time period; and a plurality of repeating time period type selection inputs providing the option to select a first type of repeating time period and a second type of repeating time period for a plurality of instances of repeating time periods. In one example, the first type of repeating time period is a work day and the second type of repeating time period is a non-work day. In another example, the user interface further includes a plurality of duration selection inputs which determine for each time block a portion of the repeating time period to which the respective time block corresponds.

In still another exemplary embodiment of the present disclosure, a method of characterizing time for physiological information within a healthcare management software system is provided. The method including the steps of: receiving a first selection of a first number of time blocks for a first day; and receiving a second selection of a second number of time blocks for a second day. In one example, the first day is classified as a first type of day and the second day is classified as a second type of day, and a third day includes the first number of time blocks if it is the first type of day and the second number of time blocks if it is the second type of day. In another example, the first number of time blocks is different than the second number of time blocks. In a variation thereof, the method further includes the steps of receiving one or more duration selections for the first number of time blocks; and receiving one or more duration selections for the second number of time blocks. In a further example, the first number of time blocks is the same as the second number of time blocks. In a variation thereof, the method further includes the steps of receiving one or more duration selections for the first number of time blocks; and receiving one or more duration selections for the second number of time blocks.

In still a further exemplary embodiment of the present disclosure, a user interface of a computing device having access to a display and a user input device is provided. The user interface including at least a first selection input to define a first number of time blocks for a first type of day; and at least a second selection input to define a second number of time blocks for a second type of day. In one example, the user interface further includes at least a third selection input to define a duration of each of the first number of time blocks and at least a fourth selection input to define a duration of each of the second number of time blocks. In a variation thereof, the third selection input is a time block divider which is positionable with the user input device relative to a linear representation of the repeating time period. In another variation thereof, the third selection input is a time block divider which is positionable with the user input device relative to a clock representation of the repeating time period.

In yet still a further exemplary embodiment of the present disclosure, a method of characterizing time for physiological information within a healthcare management software system is provided. The method including the steps of providing a plurality of time blocks for a first day, the time blocks corresponding to testing periods for blood glucose; and providing an input to define a custom textual label for at least one of the time blocks. In one example, the method further includes the steps of receiving a plurality of blood glucose values and corresponding test times; and graphically presenting the plurality of blood glucose values based on the time block including the corresponding test time. In a variation thereof, the step of graphically presenting the plurality of blood glucose values based on the time block including the corresponding test time includes the steps of graphically representing the plurality of time blocks; graphically representing the plurality of blood glucose values; and graphically representing a plurality of classifications for the plurality of blood glucose values, including a target classification. In another variation thereof, the plurality of blood glucose values and corresponding test times are provided by a blood glucose meter. In a further variation thereof, the plurality of blood glucose values and corresponding test times are provided by an infusion pump.

In yet still another exemplary embodiment of present disclosure, a method of characterizing time within a software system is provided. The method including the steps of providing a plurality of positionable time block dividers and a clock representation of a repeating time period, the plurality of positionable time block dividers being spokes emanating from a center of the clock representation of the repeating time period; receiving a position of a first time block divider; and determining a duration of a first time block and a duration of a second time block based on the received position of the first time block divider. In one example, the duration of the first time block and the duration of the second time block both being altered by rotating the first time block divider relative to the clock representation of the repeating time period. In another example, the method further includes providing for each time block a textual label.

In still yet a further exemplary embodiment of present disclosure, a user interface of a computing device having access to a display and a user input device is provided. The user interface including a graphical element being displayed on the display, the graphical element representing a repeating time period having a plurality of time blocks; and a plurality of graphical time block dividers being displayed on the display. Each of the plurality of graphical time block dividers representing the division between two adjacent time blocks and being displayed separating the two adjacent time blocks. At least a portion of the graphical time block dividers being moveable in response to an input with the user input device. In one example, the graphical element representing the repeating time period is a clock feature and each of the plurality of graphical time block dividers is a spoke extending outward from a center of the clock feature. In a variation thereof, the spoke is selectable by the user and the spoke is rotatable about the center of the clock feature to alter the time corresponding to the division between two adjacent time blocks. In another variation thereof, the user interface further includes a textual label positioned adjacent each spoke to indicate the location of the spoke within the repeating time period.

In still yet another exemplary embodiment, a method of characterizing time for physiological information within a healthcare management software system is provided. The method including the steps of providing a healthcare management software system, the healthcare management software system being able to present information based on the physiological information; and receiving a selection to include a single time block for a repeating time period. In one example, the method further includes the step of setting a duration of the single time block to the duration of the repeating time period.

Additional features and advantages of the present invention will become apparent to those skilled in the art upon consideration of the following detailed description of illustrative embodiments exemplifying the best mode of carrying out the invention as presently perceived.

BRIEF DESCRIPTION OF THE DRAWINGS

The detailed description of the drawings particularly refers to the accompanying figures in which:

FIG. 19 is an exemplary input device for setting time blocks.

FIG. 20 is another exemplary input device for setting time blocks.

FIG. 21 is a further exemplary input device for setting time blocks.

FIG. 22 is a yet another exemplary input device for setting time blocks.

FIG. 23 is still yet another exemplary input device for setting time blocks.

DETAILED DESCRIPTION OF THE DRAWINGS

Figure 1:
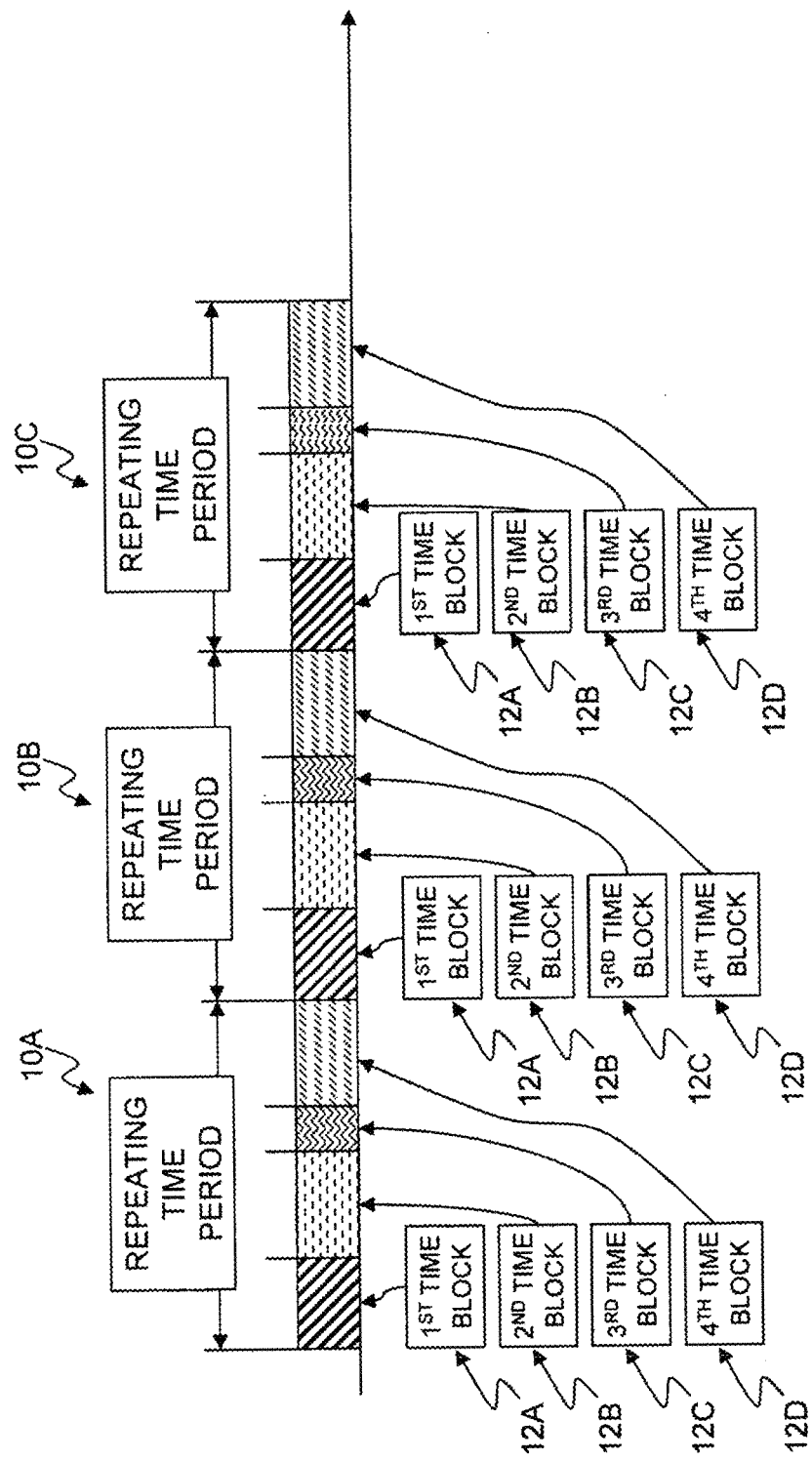
FIG. 1 is a representation of exemplary time blocks of contiguous repeating time periods.

The embodiments of the invention described herein are not intended to be exhaustive or to limit the invention to the precise forms disclosed. Rather, the embodiments selected for description have been chosen to enable one skilled in the art to practice the invention.

Concepts described below may be further explained in one of more of the co-filed patent applications entitled HELP UTILITY FUNCTIONALITY AND ARCHITECTURE U.S. Ser. No. 11/999,906, METHOD AND SYSTEM FOR GRAPHICALLY INDICATING MULTIPLE DATA VALUES U.S. Ser. No. 11/999,853, SYSTEM AND METHOD FOR DATABASE INTEGRITY CHECKING U.S. Ser. No. 11/999,856, METHOD AND SYSTEM FOR DATA SOURCE AND MODIFICATION TRACKING U.S. Ser. No. 11/999,888, PATIENT-CENTRIC HEALTHCARE INFORMATION MAINTENANCE U.S. Ser. No. 11/999,874, EXPORT FILE FORMAT WITH MANIFEST FOR ENHANCED DATA TRANSFER U.S. Ser. No. 11/999,874, GRAPHIC ZOOM FUNCTIONALITY FOR A CUSTOM REPORT U.S. Ser. No. 11/999,932, METHOD AND SYSTEM FOR SELECTIVE MERGING OF PATIENT DATA U.S. Ser. No. 11/999,859, METHOD AND SYSTEM FOR PERSONAL MEDICAL DATA DATABASE MERGING U.S. Ser. No. 11/999,772, METHOD AND SYSTEM FOR WIRELESS DEVICE COMMUNICATION U.S. Ser. No. 11/999,879, METHOD AND SYSTEM FOR ENHANCED DATA TRANSFER U.S. Ser. No. 11/999,911, COMMON EXTENSIBLE DATA EXCHANGE FORMAT U.S. Ser. No. 11/999,871, METHOD OF CLONING SERVER INSTALLATION TO A NETWORK CLIENT U.S. Ser. No. 11/999,876, METHOD AND SYSTEM FOR QUERYING A DATABASE U.S. Ser. No. 11/999,912, METHOD AND SYSTEM FOR EVENT BASED DATA COMPARISON U.S. Ser. No. 11/999,921, DYNAMIC COMMUNICATION STACK U.S. Ser. No. 11/999,934, SYSTEM AND METHOD FOR REPORTING MEDICAL INFORMATION U.S. Ser. No. 11/999,878, METHOD AND SYSTEM FOR MERGING EXTENSIBLE DATA INTO A DATABASE USING GLOBALLY UNIQUE IDENTIFIERS U.S. Ser. No. 11/999,947, METHOD AND SYSTEM FOR ACTIVATING FEATURES AND FUNCTIONS OF A CONSOLIDATED SOFTWARE APPLICATION U.S. Ser. No. 11/999, 880, METHOD AND SYSTEM FOR CONFIGURING A CONSOLIDATED SOFTWARE APPLICATION U.S. Ser. No. 11/999,894, METHOD AND SYSTEM FOR DATA SELECTION AND DISPLAY U.S. Ser. No. 11/999,896, METHOD AND SYSTEM FOR ASSOCIATING DATABASE CONTENT FOR SECURITY ENHANCEMENT U.S. Ser. No. 11/999,951, METHOD AND SYSTEM FOR CREATING REPORTS U.S. Ser. No. 11/999,905, METHOD AND SYSTEM FOR CREATING USER-DEFINED OUTPUTS U.S. Ser. No. 11/999,905, DATA DRIVEN COMMUNICATION PROTOCOL GRAMMAR U.S. Ser. No. 11/999,770, HEALTHCARE MANAGEMENT SYSTEM HAVING IMPROVED PRINTING OF DISPLAY SCREEN INFORMATION U.S. Ser. No. 11/999, 855, and METHOD AND SYSTEM FOR MULTI-DEVICE COMMUNICATION U.S. Ser. No. 11/999,866, the entire disclosures of which are hereby expressly incorporated herein by reference. It should be understood that the concepts described herein may relate to diabetes management software systems for tracking and analyzing health data, such as, for example, the Accu-Chek® 360° product provided by Roche Diagnostics. However, the concepts described herein may also have applicability to apparatuses, methods, systems, and software in fields that are unrelated to healthcare. Furthermore, it should be understood that references in this patent application to devices, meters, monitors, pumps, or related terms are intended to encompass any currently existing or later developed apparatus that includes some or all of the features attributed to the referred to apparatus, including but not limited to the Accu-Chek® Active, Accu-Chek® Aviva, Accu-Chek® Compact, Accu-Chek® Compact Plus, Accu-Chek® Integra, Accu-Chek® Go, Accu-Chek® Performa, Accu-Chek® Spirit, Accu-Chek® D-Tron Plus, and Accu-Chek® Voicemate Plus, all provided by Roche Diagnostics or divisions thereof.

Referring to FIG. 1, three instances of a repeating time period 10 are shown. The repeating time periods 10A, 10B, and 10C may have any duration. Exemplary repeating time periods 10 include a hour, a day, a week, a month, a year, or other suitable periods of time, such as a work shift of eight hours.

Each of repeating time periods 10 illustratively include four time blocks 12A-D. Each of time blocks 12A-D are contained within an instance of the repeating time period 10. Although four time blocks 12 are shown, any number of time blocks 12 may be implemented. In one embodiment, from one to twelve time blocks are contemplated. In one embodiment, different instances of repeating time period 10 may include differing numbers of time blocks 12, differing lengths of a given time block 12, or both differing numbers and lengths of time blocks 12. As such, a user may track their physiological information based on multiple time blocks during the work week and a single time block on weekends.

Figure 2:
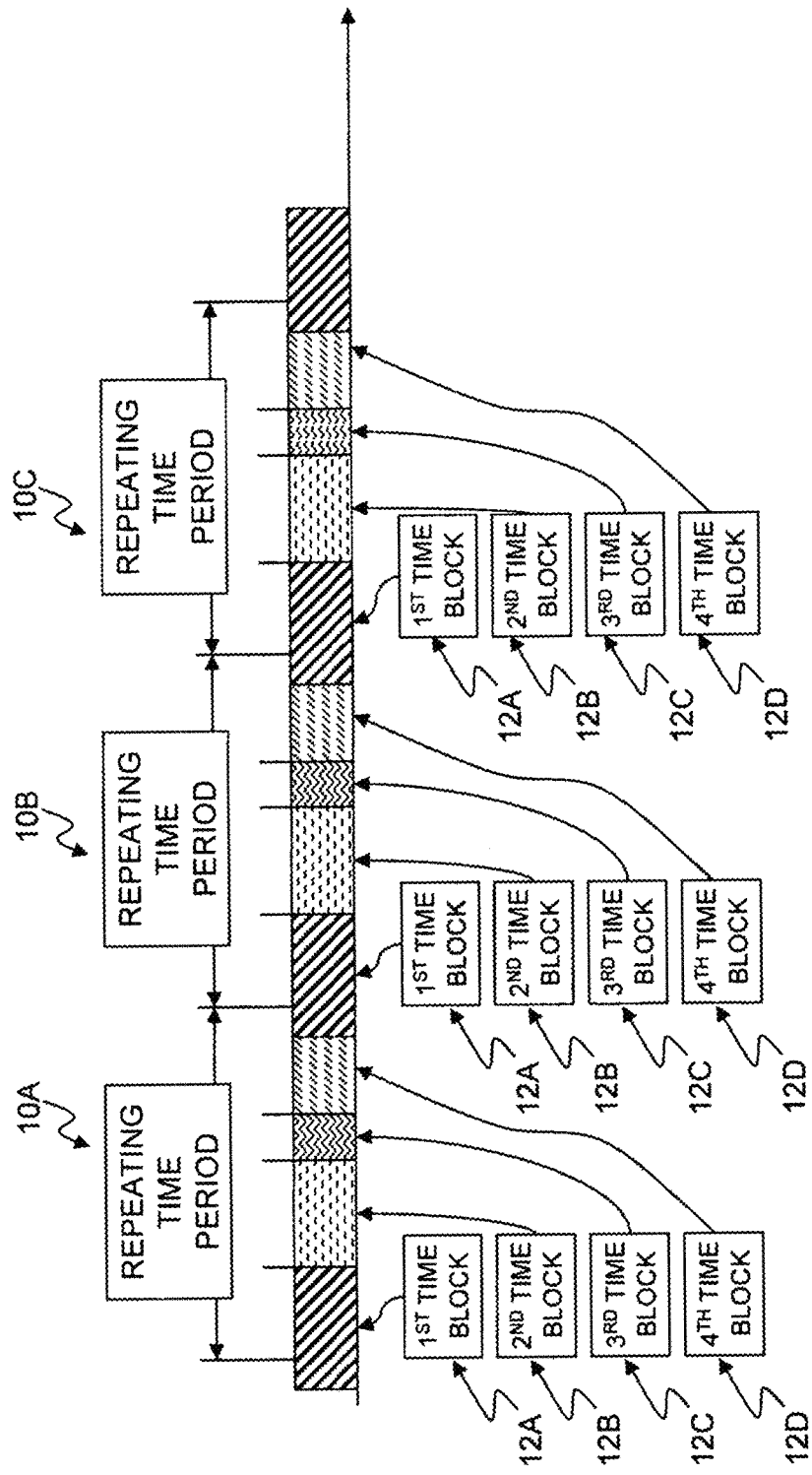
FIG. 2 is another representation of exemplary time blocks of contiguous repeating time periods.
Figure 3:
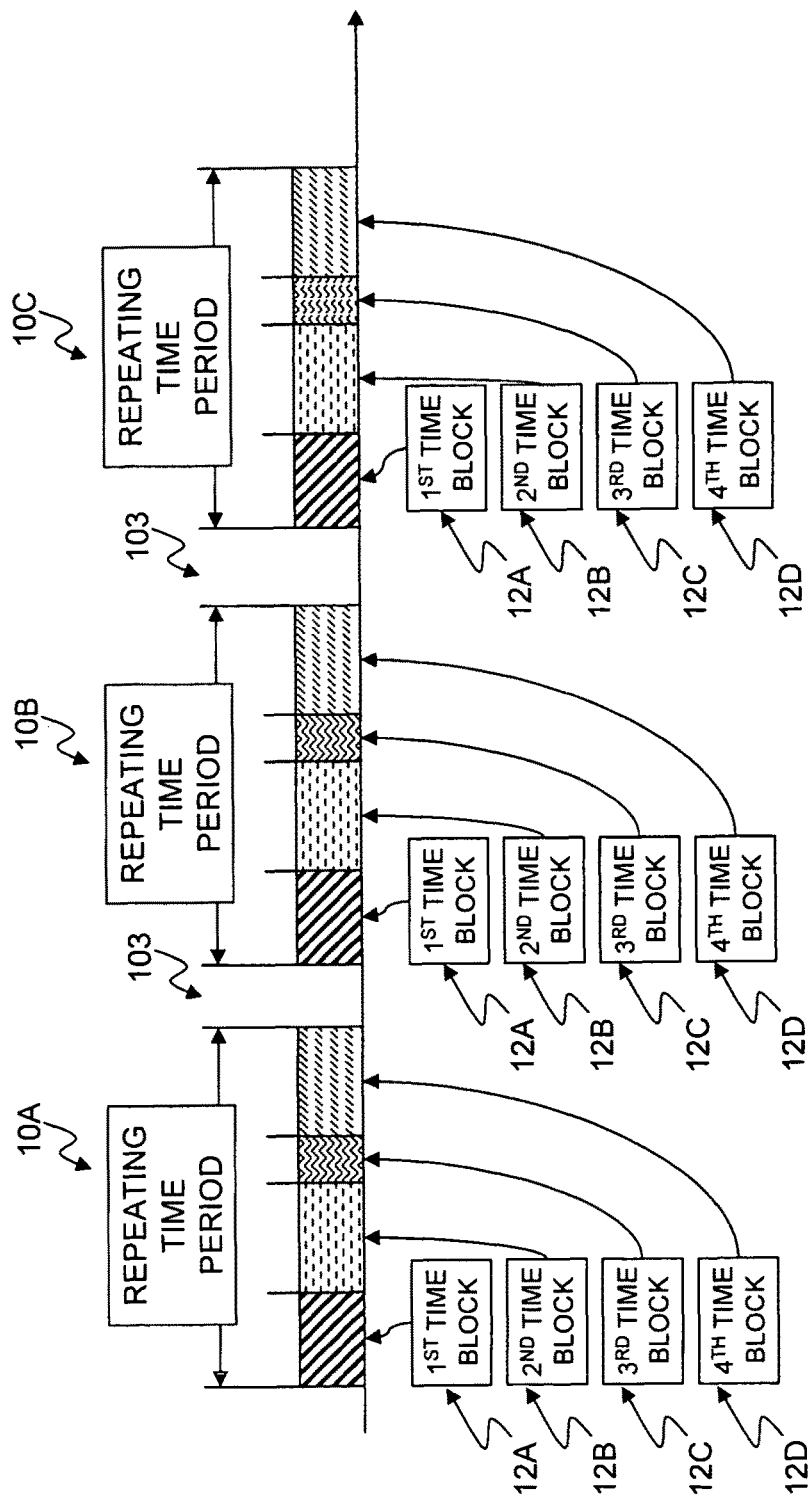
FIG. 3 is a representation of exemplary time blocks of non-contiguous repeating time periods.

As stated above, in FIG. 1 each repeating time period has self-contained continuous time blocks 12. Referring to FIG. 2, adjacent repeating time periods share a given time block 12A. This situation occurs in diabetes care applications wherein a time block of interest may be night and the repeating time period is established as a twenty-four hour day. The nighttime time block 12A often runs from approximately 8 pm in a first instance of repeating time period 10A to 6 am in a subsequent instance of repeating time period 10B. Referring to FIG. 3, adjacent repeating time periods 10 may be separated by a gap 103 in time.

The time blocks 12 and their relationship to the repeating time periods 10 and to each other may be implemented in a healthcare management software system 106. Healthcare management software system 106 may be executed by a computing device 100.

Figure 4:
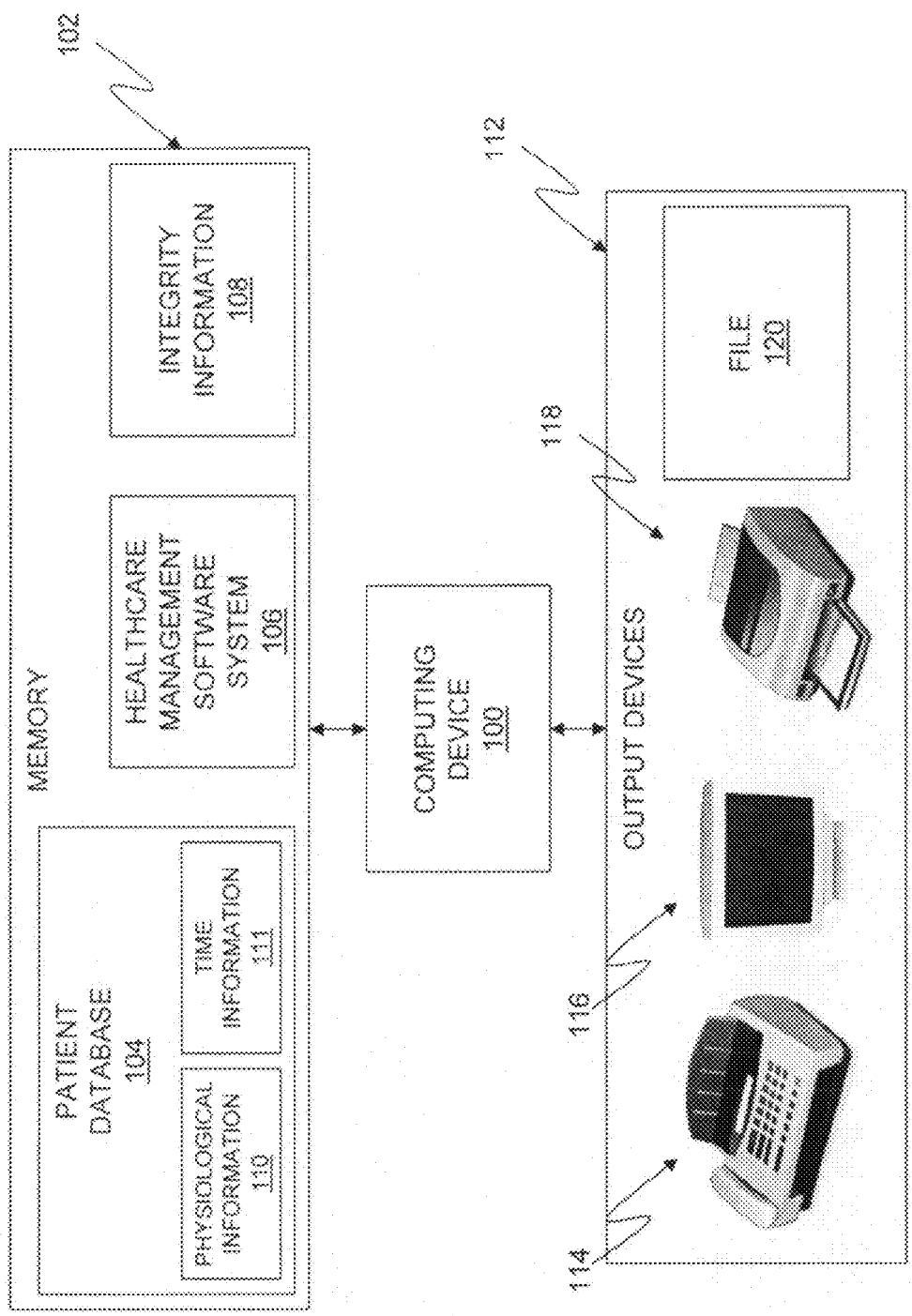
FIG. 4 is a representation of a computing device having access to one or more output devices and access to a memory containing a patient database, a healthcare management software system, and integrity information.

Referring to FIG. 4, a computing device 100 is shown. Computing device 100 may be a general purpose computer or a portable computing device. Although computing device 100 is illustrated as a single computing device, it should be understood that multiple computing devices may be used together, such as over a network or other methods of transferring data. Exemplary computing devices include desktop computers, laptop computers, personal data assistants ("PDA"), such as BLACKBERRY brand devices, cellular devices, tablet computers, infusion pumps, blood glucose meters, or an integrated device including a glucose measurement engine and a PDA or cell phone.

Computing device 100 has access to a memory 102. Memory 102 is a computer readable medium and may be a single storage device or multiple storage devices, located either locally with computing device 100 or accessible across a network. Computer-readable media may be any available media that can be accessed by the computer 102 and includes both volatile and non-volatile media. Further, computer readable-media may be one or both of removable and non-removable media. By way of example, and not limitation, computer-readable media may comprise computer storage media. Exemplary computer storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store the desired information and which can be accessed by the computing device 100.

Memory 102 includes one or more patient databases 104 and healthcare management software system 106. Patient databases 104 include physiological information 110 related to one or more patients. Exemplary physiological information includes blood glucose values, A1c values, Albumin values, Albumin excretion values, body mass index values, blood pressure values, carbohydrate values, cholesterol values (total, HDL, LDL, ratio) creatinine values, fructosamine values, HbA1values, height values, insulin dose values, insulin rate values, total daily insulin values, ketone values, microalbumin values, proteinuria values, heart rate values, temperature values, triglyceride values, and weight values.

Physiological information 110 may be provided directly by the patient, provided by a caregiver, and/or provided by one or more sensors. Exemplary sensors are provided in insulin pumps and glucose meters. The physiological information 110 is related to time information 111 which corresponds to the time the measurement was taken or represents a period of time within which a measurement was taken.

Healthcare management software system 106 includes instructions which when executed by computing device 100 present physiological information 110 or information based on physiological information 110 to an output device 112. Exemplary information presented by healthcare management software system 106 to output device 112 include diaries of blood glucose values and reports showing a plurality of blood glucose values and the times or times blocks to which the blood glucose values correspond. Exemplary reports include standard day reports (see FIG. 14) wherein the blood glucose values are grouped according to the time of day taken, standard week reports (see FIG. 15) wherein the blood glucose values are grouped according to the day of the week taken, trend graphs (see FIG. 16) to illustrate temporal trends in blood glucose values, and other suitable reports and/or graphs.

Computing device 100 has access to output device 112. Exemplary output devices 112 include fax machines 114, displays 116, printers 118, and files 120. Files 120 may have various formats. In one embodiment, files 120 are portable document format (PDF) files. In one embodiment, files 120 are formatted for display by an Internet browser, such as Internet Explorer available from Microsoft of Redmond, Wash., and may include one or more of HyperText Markup Language ("HTML"), or other formatting instructions. In one embodiment, files 120 are files stored in memory 102 for transmission to another computing device and eventual presentation by another output device or to at least influence information provided by the another output device.

Figure 5:
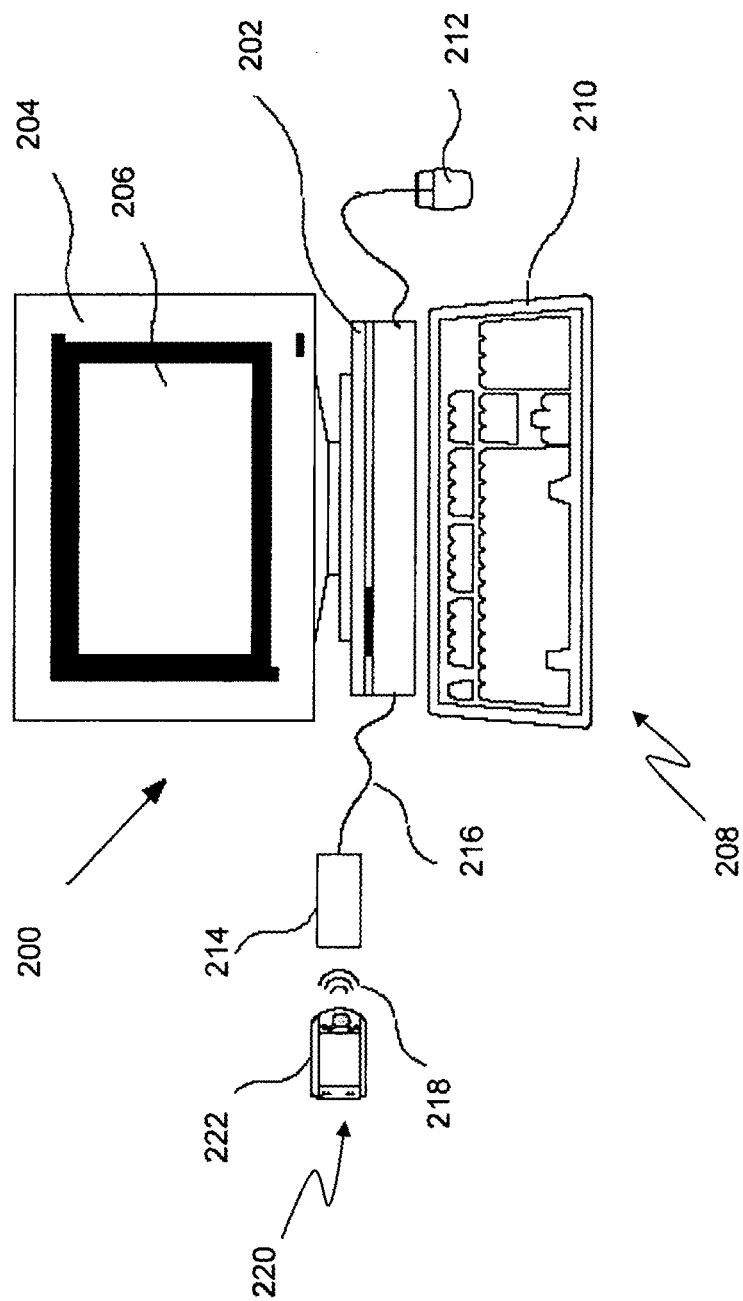
FIG. 5 is a representation of an exemplary computing device receiving information from a remote medical device.

In one embodiment, healthcare management software system 106 is a diabetes care software which is loaded on a computing device 100. The diabetes care software interacts with a blood glucose meter to receive blood glucose values and other physiological information 110. The diabetes care software system then is able to present the blood glucose values to the patient or caregiver for review. Referring to FIG. 5, an exemplary computing device 200 is shown. Computing device 200 is a personal computer 202. Computing device 200 is coupled to an output device 204, illustratively a display screen 206. Computing device 200 is further coupled to a plurality of input devices 208. A first exemplary input device is a keyboard 210. A second exemplary input device is a mouse 212. A third exemplary input device is a modulated signal transceiver 214, in electronic communication with computer 202 through a cable 216. Transceiver 214 is configured to transmit and receive a modulated signal 218 and to establish communications to and from a remote device 220. An exemplary remote device 220 is a blood glucose meter 222. Another exemplary remote device is an infusion pump.

In one embodiment, blood glucose meter 222 is assigned to a patient and associated with that patient in healthcare management software system 106. Thus, when physiological information 110 from blood glucose meter 222 is transferred to healthcare management software system 106, the physiological information 110 from blood glucose meter 222 automatically populates database records in patient database 104 relating to that patient along with the time information 111 related to the physiological information 110. In one embodiment, meter 222 provides blood glucose values and test times corresponding to the blood glucose values. The test times including both day and time information.

Although a blood glucose meter 222 is shown, any medical device may be implemented having data to be used by healthcare management software system 106. Medical devices 220 are devices capable of recording patient data and transferring data to software applications and may include monitors which record values of measurements relating to a patient's state and information such as the time and date when the measurement was recorded. Medical devices may also be devices configured to provide medications to patients such as, for example, insulin pumps. These devices, generally, record dosage amounts as well as the time and date when the medication was provided. It should be understood that the functionality of medical device 220 may be included within an exemplary computing device 100.

Computing device 200 may be used by the patient, a caregiver, or anyone having relevant data pertaining to a patient. Computing device 200 may be located in a patient's home, a healthcare facility, a drugstore, a kiosk, or any other convenient place. In an alternative embodiment, computing device 200 may be connected to a remote computing device, such as at a caregiver's facility or a location accessible by a caregiver, and physiological information 110 in patient database 104, or the complete patient database 104, may be transferred between them. In this embodiment, computing device 200 and the remote device are configured to transfer physiological information 110 and/or time information 111 in patient database 104, or the complete patient database 104, between them through a data connection such as, for example, via the Internet, cellular communications, or the physical transfer of a memory device such as a diskette, USB key, compact disc, or other portable memory device. Computing device 200 and/or the remote device, may be configured to receive physiological information 110 from a medical device or, alternatively, to receive physiological information 110 transferred from the other of computing device 200 and the remote device.

Figure 6:
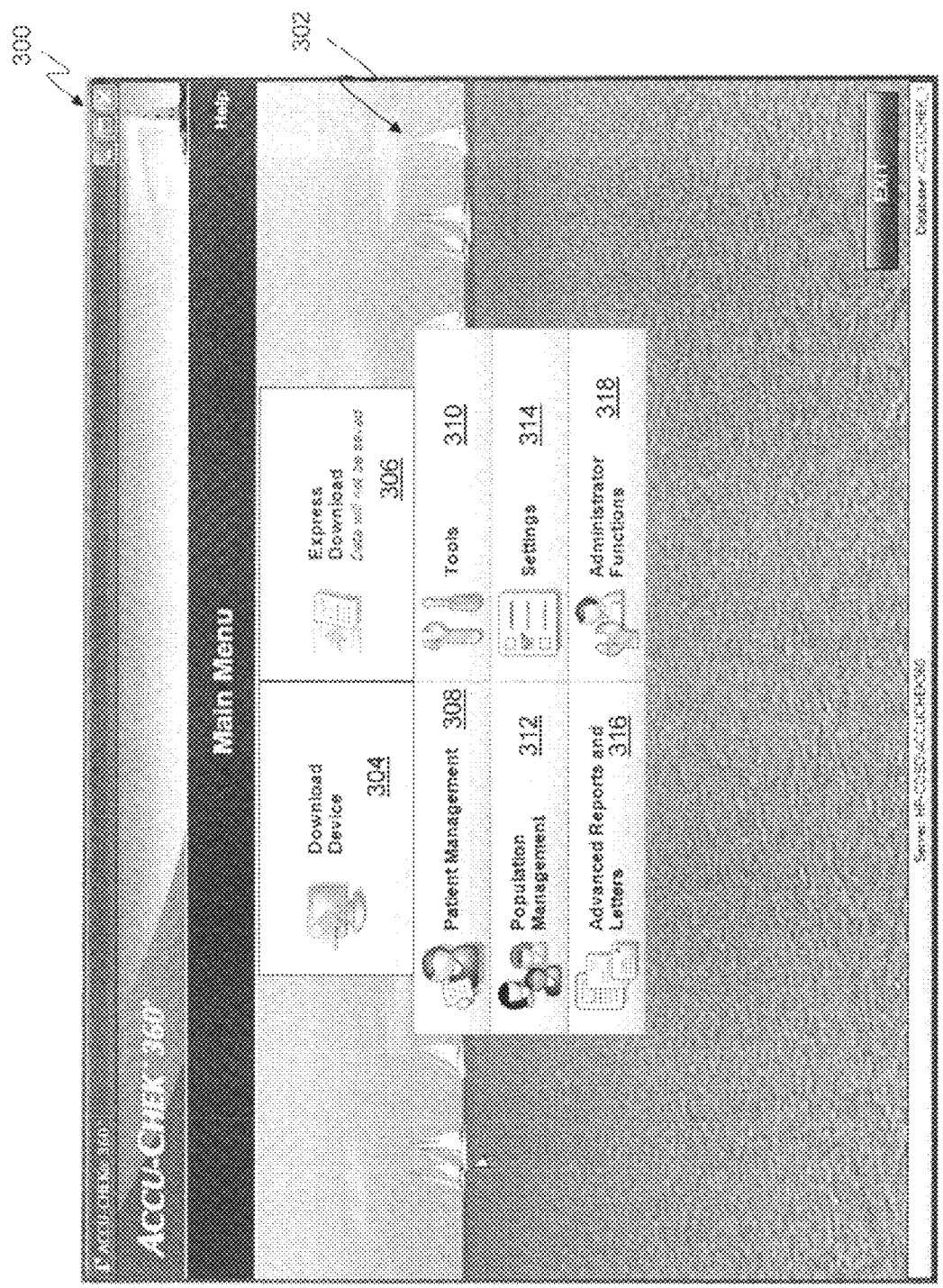
FIG. 6 is an exemplary main menu screen of a user interface of a healthcare management software system.
Figure 7:
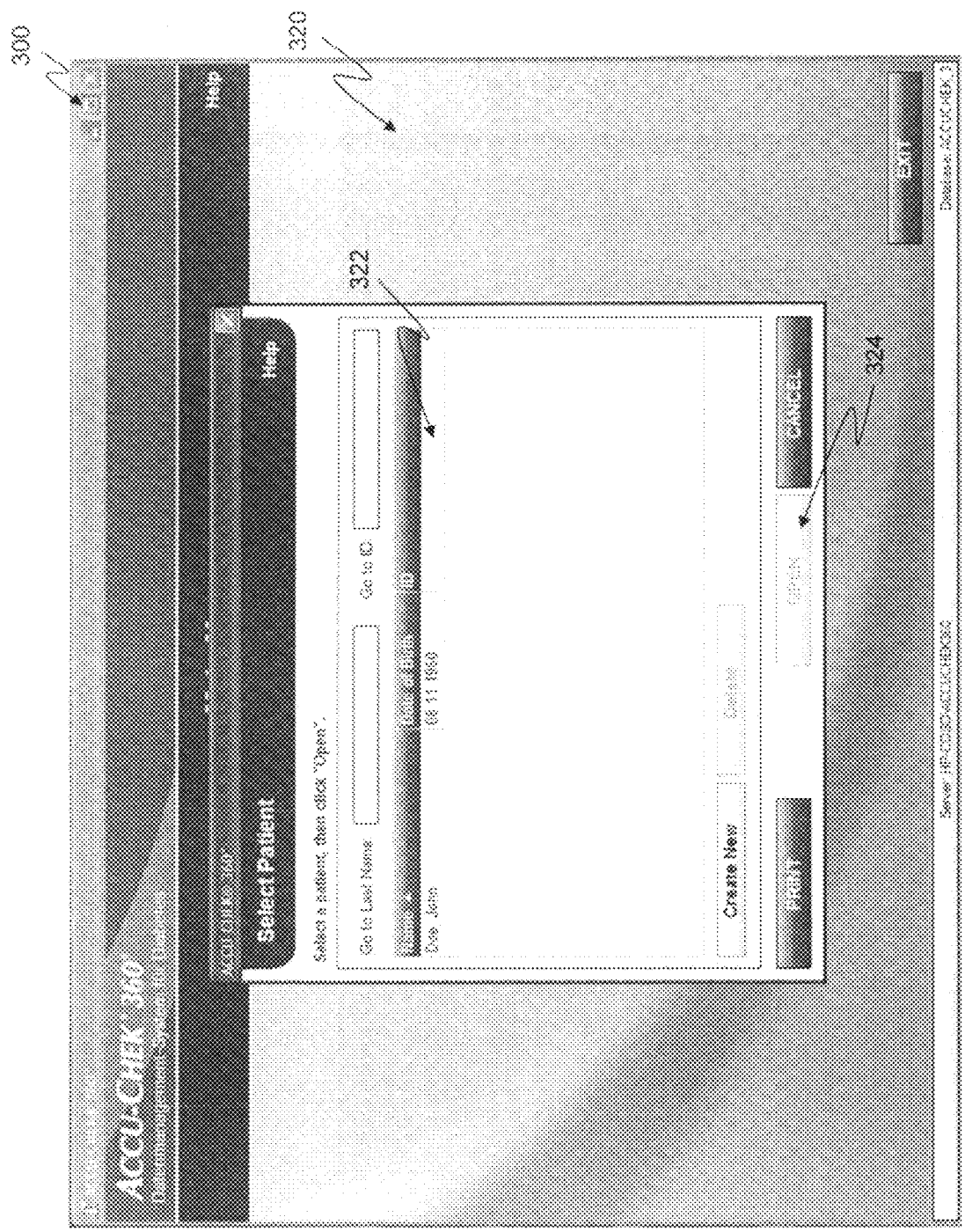
FIG. 7 is an exemplary patient selection screen of a user interface of a healthcare management software system.

An exemplary user interface 300 of an exemplary healthcare management software system 106 which may be executed by computing devices 100, 200 is shown in FIGS. 6-18. Referring to FIG. 6, a main menu screen 302 of user interface 300 is shown. Screen 302 includes a first selection input 304 for downloading physiological information 110 and associated time information 111 from glucose meter 222 for inclusion in patient database 104. A second selection input 306 is provided for downloading physiological information 110 and associated time information 111 from glucose meter 222, but not for storing in patient database 104. A third selection input 308 is provided for managing physiological information 110 in patient database 104 including generation of reports and entry of additional physiological information 110. It is under this option that a user may select the number of time blocks and other information related to the repeating time periods. In the embodiment of healthcare management software system 106, the repeating time period is a twenty-four hour day and the time blocks are divisions of the twenty-four hour day which may cross-over into adjacent twenty-four hour day periods.

Returning to FIG. 6, a fourth selection input 310 is provided for a tools menu. The tools menu includes selection inputs for importing physiological information 110, exporting physiological information 110, clearing physiological information 110 on a meter 222 in communication with healthcare management software system 106, setting the date and time of a meter 222 in communication with healthcare management software system 106, exporting physiological information 110 to a CSD file, determining by brand the amount of testing data communicated from a plurality of meters 222. As such, a caregiver may see that for meter brand A 3000 entries of testing data for 20 patients were downloaded while for meter brand B 1000 entries of testing data for 20 patients were downloaded. The caregiver may then have a clearer picture of the brand of meter that their patients are using more frequently.

A fifth selection input 312 is provided for population management. Exemplary population management includes the ability to create groups based on either query groups where the database is queried to find patients that satisfy a criteria or a static group query. An exemplary static query group is a drug effectiveness group. The patients included in the drug effectiveness group are known and should not be allowed to change based on a query criteria. A sixth selection input 314 is provided for changing the settings of healthcare management software system 106. A seventh selection input 316 is provided for advanced reports and letters which allows a user to create custom reports through a report template builder and a letter builder which generates letters to patients in the database meeting a given criteria. Exemplary criteria include recent office visit, upcoming testing, and other criteria. A eighth selection input 318 is provided for administrator functions.

Upon selection of the third selection input 308, screen 320 (see FIG. 7) is presented on user interface 300. Healthcare management software system 106 presents the user with a listing of patients 322 from which to select. A patient is selected by highlighting the name of the patient and selecting the OPEN selection input 324. Once a patient is selected, screen 330 (see FIG. 8) is presented and a user may perform a multitude of tasks with healthcare management software system 106. The name of patient database 104 is provided as textual label 332 and the path associated with the patient database 104 is provided as textual label 334.

Figure 8:
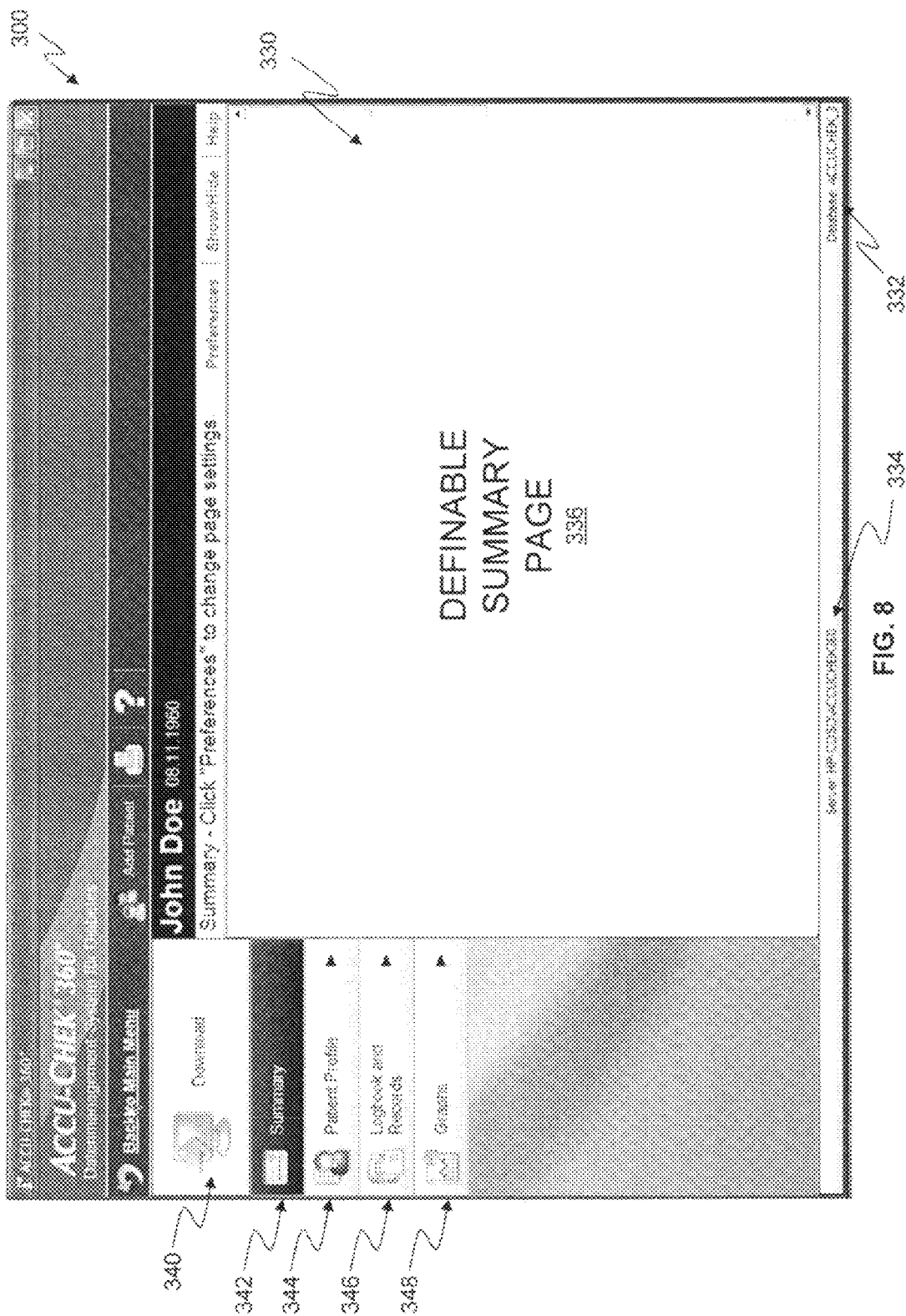
FIG. 8 is an exemplary patient summary screen of a user interface of a healthcare management software system.

Referring to FIG. 8, a patient summary page 336 is provided. Patient summary page 336 is a customizable page wherein one or more of caregiver visit notes, alerts (such as past due items), reports, graphs, logbooks, and records may be presented as a snapshot of the patient.

A plurality of selection inputs are also provided on screen 330. A user may return to screen 320 by selecting selection input 338. A selection input 340 functions the same as selection input 304 on screen 302 and is selected to download physiological information 110 and time information 111 from meter 222. Selection input 342 is provided for a patient summary. Upon selection patient summary, a user may edit the items presented as summary page 336. Selection input 344 is provided for patient profile information. Selection input 346 is provided for logbooks and records. Upon selecting logbooks and records, a user may enter information such as blood glucose values, insulin usage information, medications, medication dosages and dates, lab values, blood pressure values, weight, health complications (symptoms and severity), types of care education the patient receives, visit notes, exercise information, and other information. A selection input 348 is provided for graphs. Upon selecting graphs, a user may one of a plurality of graphs. A selection input 350 (see FIG. 9) is provided for favorite reports. Upon selecting favorite reports, a user may setup a customized graph or report that they use to analyze blood glucose values and other physiological information 110.

Figure 9:
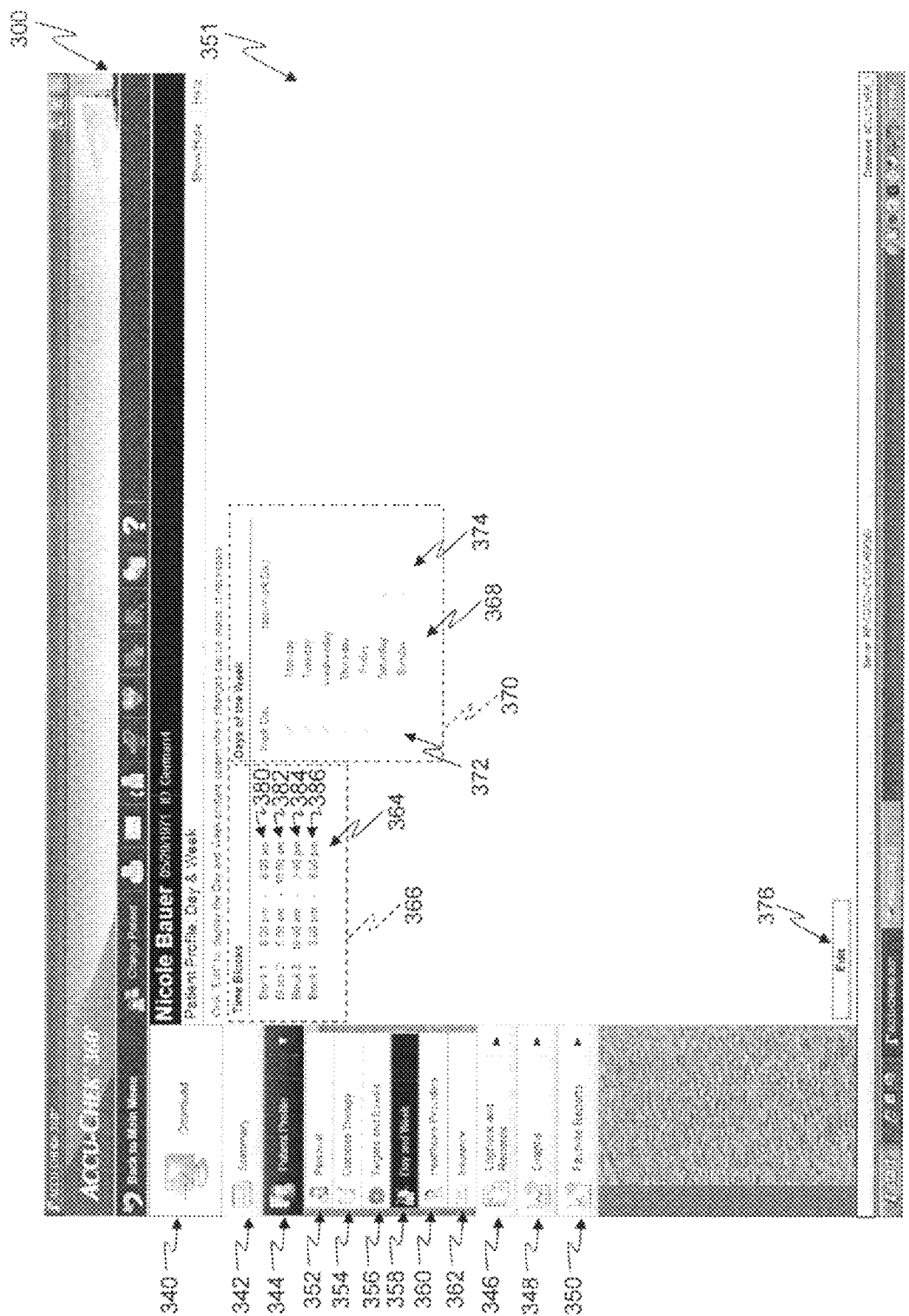
FIG. 9 is an exemplary day and week summary screen of a user interface of a healthcare management software system.

Referring to FIG. 9, screen 351 is shown in response to the selection of selection input 344. FIG. 9 includes selection inputs 352, 354, 356, 358, 360, and 362. Selection input 352 is provided for patient personnel information. Upon selecting patient personnel information, a user may provide patient name, date of birth, type of diabetes, contact information, emergency contact information, and other information. Selection input 354 is provided for diabetes therapy information. Selection input 356 is provided for targets and events information. Upon selecting targets and events information, a user may blood glucose targets and other information. Selection input 358 is provided for day and week information. Selection input 360 is provided for healthcare providers information. Selection input 362 is provided for insurance information.

In FIG. 9 selection input 358 corresponding to day and week information has been selected. Textual information 364 regarding the number and corresponding times for four time blocks 380, 382, 384, 386 is displayed in region 366. Textual information 368 regarding the classification of each of the days of the week as either work days or non-work days is provided in region 370. The classification of each day is represented by a checkmark. A checkmark in column 372 indicates a first type of day, illustratively a work day. A checkmark in column 374 indicates a second type of day, illustratively a non-work day. Further, a selection input 376 is provided to permit the user to change the number of time blocks, the time period for a given time block, and/or the classification of each day of the week.

Upon selection of selection input 376, screen 400 is shown. Screen 400 includes a selection input 402, which permits a user to change the number of time blocks that are provided for each day of the week. In the illustrated embodiment, selection input 402 is shown as a drop-down box. However, other suitable selection inputs may be used, including a fill-in box, option buttons, a scrollable list, and other suitable selection inputs. In one embodiment, multiple selection inputs 402 are provided, one for each type of repeating time period.

In the illustrated embodiment, the number of time blocks, illustratively time blocks 380, 382, 384, and 386, is constant for every day of the week. In the illustrated embodiment, a twenty-four hour day is the repeating time period. In one embodiment, the number of time blocks may be different for differing days of the week. For instance, the work days may have a first number of time blocks, while the non-work days would have a second number of time blocks. Further, in one embodiment, the duration of time blocks differs from day to day, such as based on the type of day.

By changing the number of time blocks, the user is able to control the time periods in which they want to track their blood glucose values or other physiological information 110 or at least classify their blood glucose values or other physiological information 110. Traditional software systems predefine that a day has a set number of time periods and a user must make their routine fit that regiment of time blocks. Healthcare management software system 106 permits a user to track a variable number of time blocks. In one embodiment, a user may select from 2 to 12 time blocks for a day. In another embodiment, a user may select from 2 to 24 time blocks for a day. In a further embodiment, a user may select from 2 to 48 time blocks for a day. As such, if a user does not eat breakfast, the first time block of the day may last until lunch. Further, if a user exercises every afternoon, a time block may be defined for pre-exercise time, one for exercise time, and one for post-exercise time. In one embodiment, a user may also specify the text of the textual labels for one or more of the time blocks. As such, a user could specify the text to be pre-exercise, post-exercise, if desired.

Figure 10:
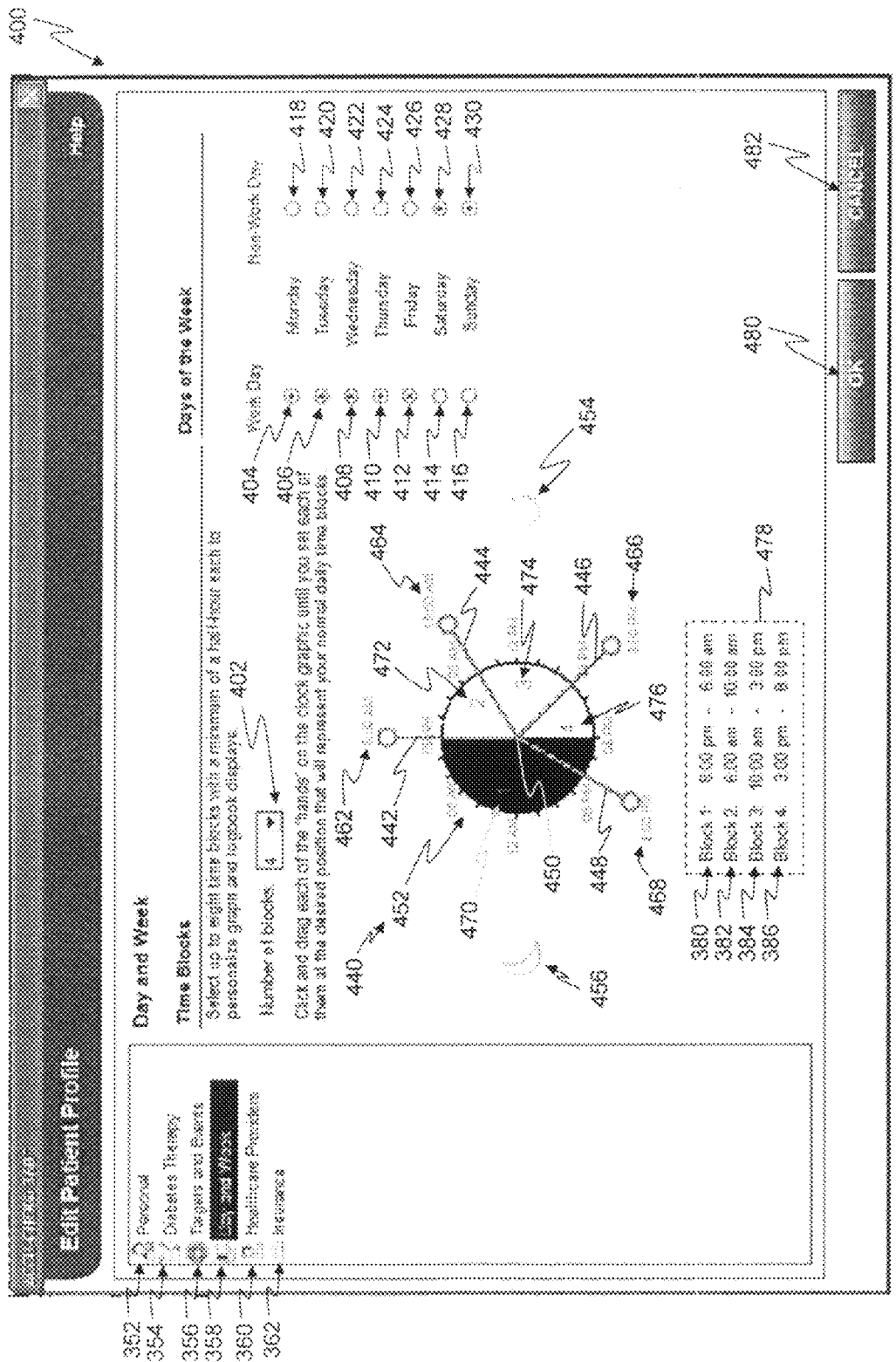
FIG. 10 is an exemplary edit screen of a user interface of a healthcare management software system for setting time blocks for a day and types of days.

Also shown on FIG. 10 are a plurality of inputs 404 through 430 whereby a user may designate each of the seven days of the week (seven instances of the repeating period) as either a work day or a non-work day. This permits flexibility for a user to track differences in blood glucose values for different classes of days and also permits healthcare management software system 106 to be tailored to work weeks other than Monday through Friday. Work days and non-work days are examples of types of repeating time periods. Other types of repeating time periods may also be implemented, such as school days and non-school days.

Although two types are illustrated, it is contemplated to include three or more types of repeating time periods. In one embodiment, a user may have two different work day types and a non-work day type. For example, for a first work day type the user may have a longer shift than the second work day type. In one embodiment, a user may specify time blocks for each type of repeating time period and/or provide a descriptive text for the textual label for one or more time blocks.

Also shown on FIG. 10, is a selection input 440 through which a user may select the time periods corresponding to each time block. Selection input 440 consists of four selection spokes 442 through 448. There are four selection spokes because the user has selected four time periods. Each of selection spokes 442-448 emanate from a common point 450. Centered on point 450 is a representative clock face 452 including textual labels to indicate the hours of the day. As shown in FIG. 10, the representative clock face 452 passes through a complete 24-hour period as opposed to a 12-hour period on a standard clock. Also, visual icons 454 and 456 are provided to generally indicate which portions of clock face 452 correspond to daylight hours and which portions correspond to nighttime hours. If a month was the repeating time period, then the representative clock 452 may include textual labels to indicate the days of the month.

Each of spokes 442-448 includes a corresponding textual label 462 through 468. Textual labels 462 through 468 indicate the time corresponding to the location of the corresponding spoke. The time period provided between two adjacent spokes is the time period for each of the time blocks 380-386. Textual labels 470 through 476 are provided to indicate the location of each time block. Also, the time periods corresponding to each time block 380-386 are provided in region 478 directly below selection input 440. As illustrated in FIG. 10, block 1 is defined between spokes 448 and 442 and corresponds to the time period of 8:00 p.m. through 6:00 a.m. Time period 2 corresponds to the time between spokes 442 and 444 and corresponds to the time period of 6:00 a.m. through 10:00 a.m. Time period 3 corresponds to the time between spokes 444 and 446 and corresponds to the time period of 10:00 a.m. through 3:00 p.m. Time period 4 corresponds to the time between spokes 446 and 448 and corresponds to the time period of 3:00 p.m. through 8:00 p.m. Once the user has made the appropriate changes to the number of time blocks through selection input 402 or the time periods corresponding to a given time block through selection input 440 or the classification of one of the days of the week through selection inputs 404-430, the user may select selection input 480 to accept the changes or selection input 482 to abort the changes.

Figure 11:
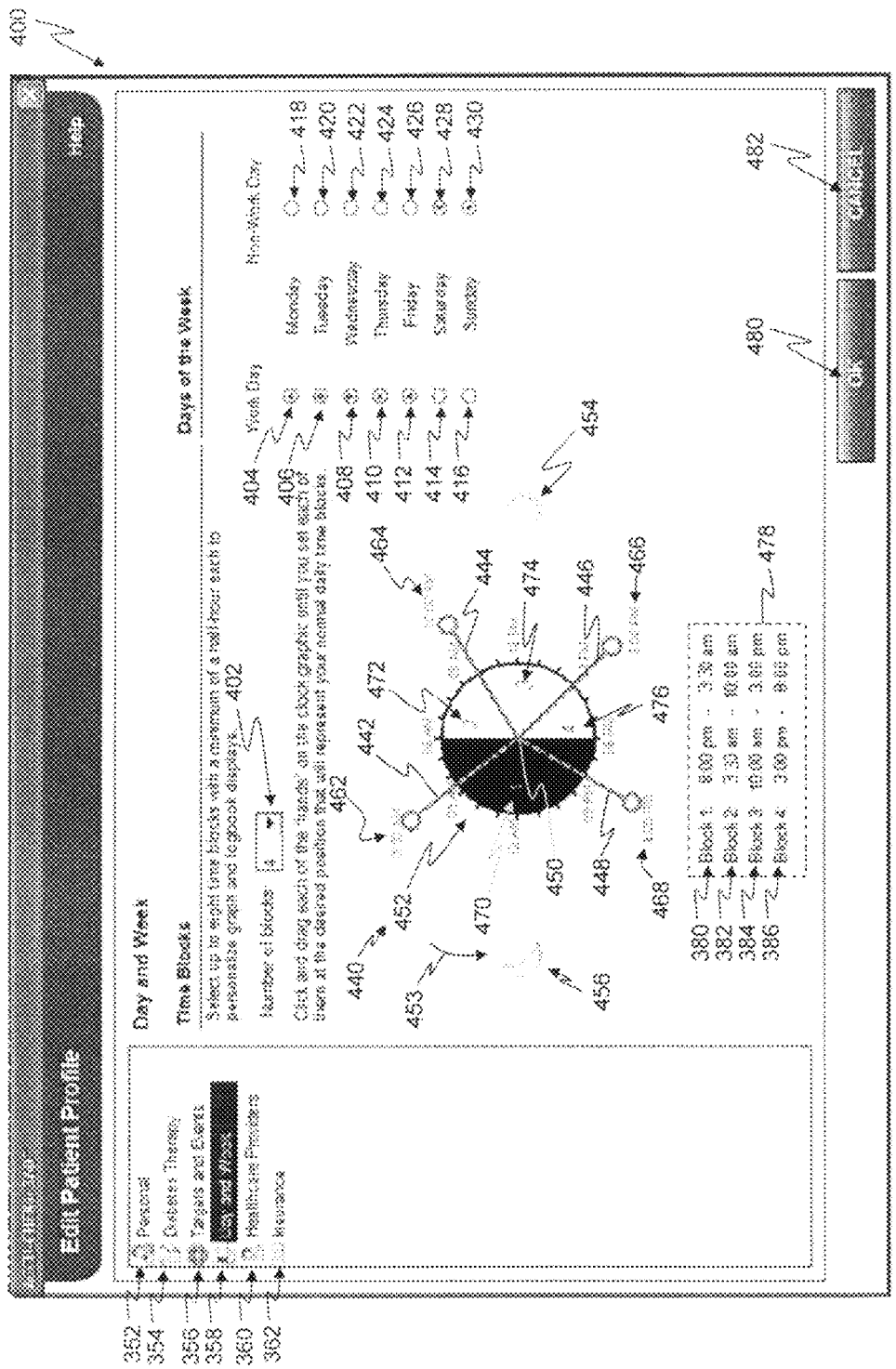
FIG. 11 is an exemplary edit screen of a user interface of a healthcare management software system for setting time blocks for a day and types of days having a time block divider moved from a prior location in FIG. 10.

Referring to FIG. 11, to change the time periods corresponding to a given time block, a user may select one of the spoke inputs 442 through 448 and drag its location to a desired position. In one embodiment (using personal computer 202), the user selects a spoke by positioning the cursor corresponding to the mouse 212 on the spoke, depressing the left button on the mouse, and moving the mouse to move the location of the spoke. As shown in FIG. 11, the location of spoke 442 has been changed from 6:00 a.m. in FIG. 10 to 3:30 a.m. in FIG. 11. Spoke 442 is still emanating from center 450 and has been rotated in direction 453. In one embodiment, when spoke 442 is selected a "+" icon (indicating increasing the time period) appears to the right of spoke 442 and a "−" icon (indicating decreasing the time period) appears to the left of spoke 442.

As shown in FIG. 11, the text of textual label 462 has been updated to reflect this change as well as the information provided in region 478 for the time periods corresponding to the time blocks 380-386. As shown, by moving spoke 442 time block 1 has been shortened while time block 2 has been lengthened. In one embodiment, the granularity of the movement of spokes 442 and 448 is in increments of 30 minutes. In other embodiments, the granularity of spoke 442 through 448 may be less than 30 minutes or greater than 30 minutes.

Further, the rotation of spoke 442 in direction 453 does not affect the position of spoke 448 until spoke 442 is only one increment of granularity away from spoke 448, illustratively a half an hour. At this point, time block 1 has the minimum duration of 30 minutes. Further, movement of spoke 442 in direction 453 will cause not only the movement of spoke 442, but also the movement of spoke 448. These two spokes will move together until spoke 448 is within 30 minutes of spoke 446. At this time, both time period 1 and time period 4 are at the minimum time duration of 30 minutes. Further movement of spoke 442 in direction 453 will cause the movement of not only spoke 442, but also spokes 446 and 448. This will continue until spoke 446 is at 30 minutes from spoke 444. At this point, time periods 1, 4, and 3 are each at 30 minutes. The further movement of spoke 442 in direction 453 will cause not only the movement of spoke 442, but also spokes 444, 446, and 448.

Figure 12:
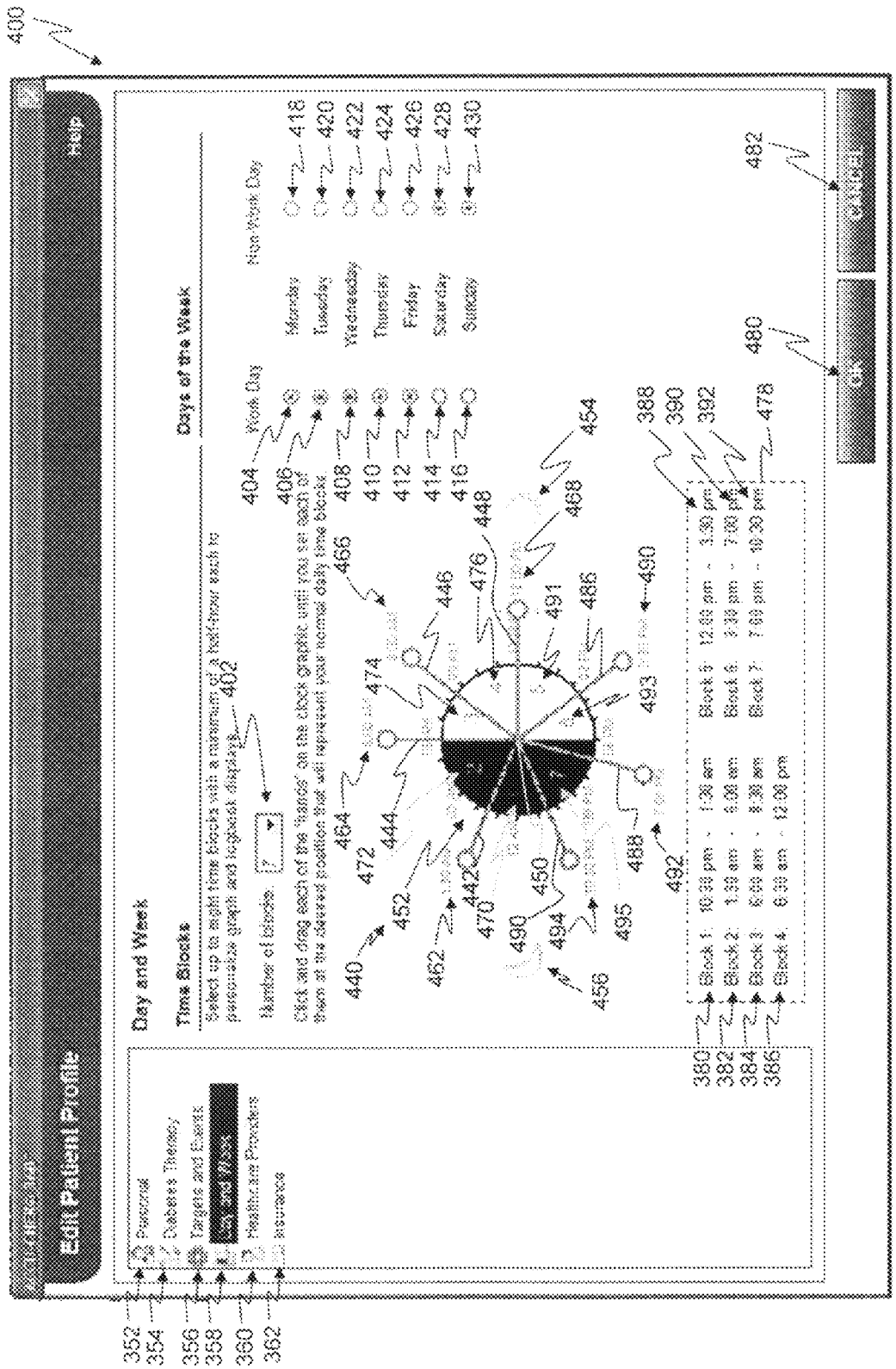
FIG. 12 is an exemplary edit screen of a user interface of a healthcare management software system for setting time blocks for a day and types of days having additional time blocks added relative to FIG. 10.
Figure 13:
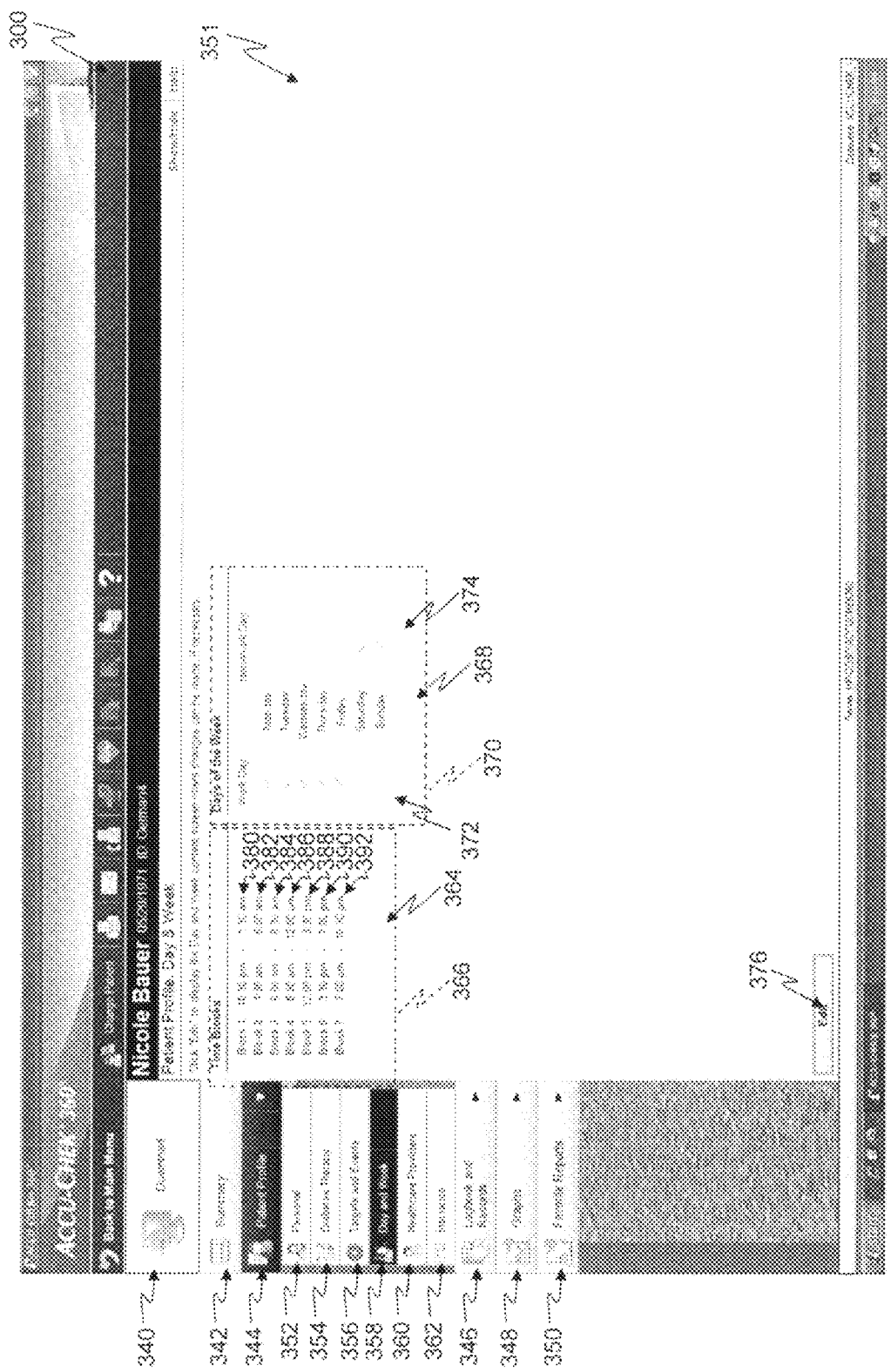
FIG. 13 is an exemplary day and week summary screen of a user interface of a healthcare management software system showing the selections made in FIG. 12.

Referring to FIG. 12, selection input 402 has been changed to reflect seven time blocks 380, 382, 384, 386, 388, 390, and 392, as opposed to the four time blocks 380, 382, 384, 386 selected in FIG. 10. As shown by selection input 440, along with spokes 442 through 448, additional spokes 486-490 are also shown. Further, the textual information in region 478 has been updated to reflect the time periods of each of the seven time blocks 380, 382, 384, 386, 388, 390, and 392. Also, additional textual labels 490, 492, and 494 have been added to indicate the time associated with spokes 486, 488, and 490 and textual labels 491, 493, and 495 have been added to indicate the location of time blocks 388, 390, and 392.

Upon selection of user input 480, health care management software system 106 presents screen 351 to the user. As seen in screen 351, the textual information in region 366 has been updated to reflect the selections for the seven time blocks 380, 382, 384, 386, 388, 390, and 392, and the textual information in region 370 remains unchanged because of the absence of changes of the state of selection inputs 404-430.

Although selection input 440 is shown for adjusting the time periods of time blocks 380, 382, 384, 386, 388, 390, and 392, other suitable selection inputs may be used. Exemplary selection inputs include fill-in fields, list boxes, drop-down lists, option buttons, toggles, check boxes, and other suitable selection inputs. Additional exemplary selection inputs are shown in FIGS. 19-24.

Referring to FIG. 19, a selection input 650 is shown. Selection input 650 includes the same positionable spokes and corresponding textual labels of the spokes as selection input 440. Illustratively six time periods are shown divided by spokes 442, 444, 446, 448, 486, and 488. Selection input 650 includes a clock representation 652. Clock representation 652 differs from clock representation 452 in that clock representation 652 does not include a visual indicator of daytime and nighttime, as represented in clock representation 452 by the half white and half black face.

Referring to FIG. 20, a selection input 670 is shown. Selection input 670 includes the same positionable spokes and corresponding textual labels of the spokes as selection input 440. Illustratively, six time periods are shown divided by spokes 442, 444, 446, 448, 486, and 488. Selection input 670 also includes a clock representation 452. Selection input 670 differs from selection input 440 in that it includes handles 672, 674, 676, 678, 680, and 682 which include lines to indicate to the user that the handles may be used to move the spokes.

Referring to FIG. 21, a selection input 684 is shown. Selection input 684 is the same as selection input 670. Selection input 684 has associated therewith textual labels 470, 472, 474, 476, 491, and 493 to indicate the time block of each region of clock representation 452.

Referring to FIG. 22, a selection input 690 is shown. Selection input 690 includes the same positionable spokes and corresponding textual labels of the spokes as selection input 440. Illustratively six time periods are shown divided by spokes 442, 444, 446, 448, 486, and 488. Selection input 690 also includes a clock representation 452. Selection input 690 differs from selection input 440 in that it includes textual labels 692, 694, 696, 698, 700, and 702 instead of textual labels 470, 472, 474, 476, 491, and 493 to indicate the time block of each region of clock representation 452. Textual labels 692, 694, 696, 698, 700, and 702 move with the respective spoke 442, 444, 446, 448, 486, and 488.

Referring to FIG. 23, a selection input 720 is shown. Selection input 720 includes a linear representation 722 of the repeating time period, illustratively a twenty-four hour day. Linear representation 722 includes a textual label 724 indicating the major divisions of the repeating time period.

Selection input 720 further includes sliders 726, 728, 730, 732, 734, and 736 which operate as time block dividers in the same manner that spokes 442, 444, 446, 448, 486, and 488 operate as time block dividers. Sliders are moveable in directions 735 and 737 to adjust the times included in a respective time period. The region between two adjacent sliders corresponds to a time block. Each of sliders 726, 728, 730, 732, 734, and 736 have a respective textual label 738, 740, 742, 744, 746, an 748 indicating the time corresponding to the position of the slider.

Figure 24:
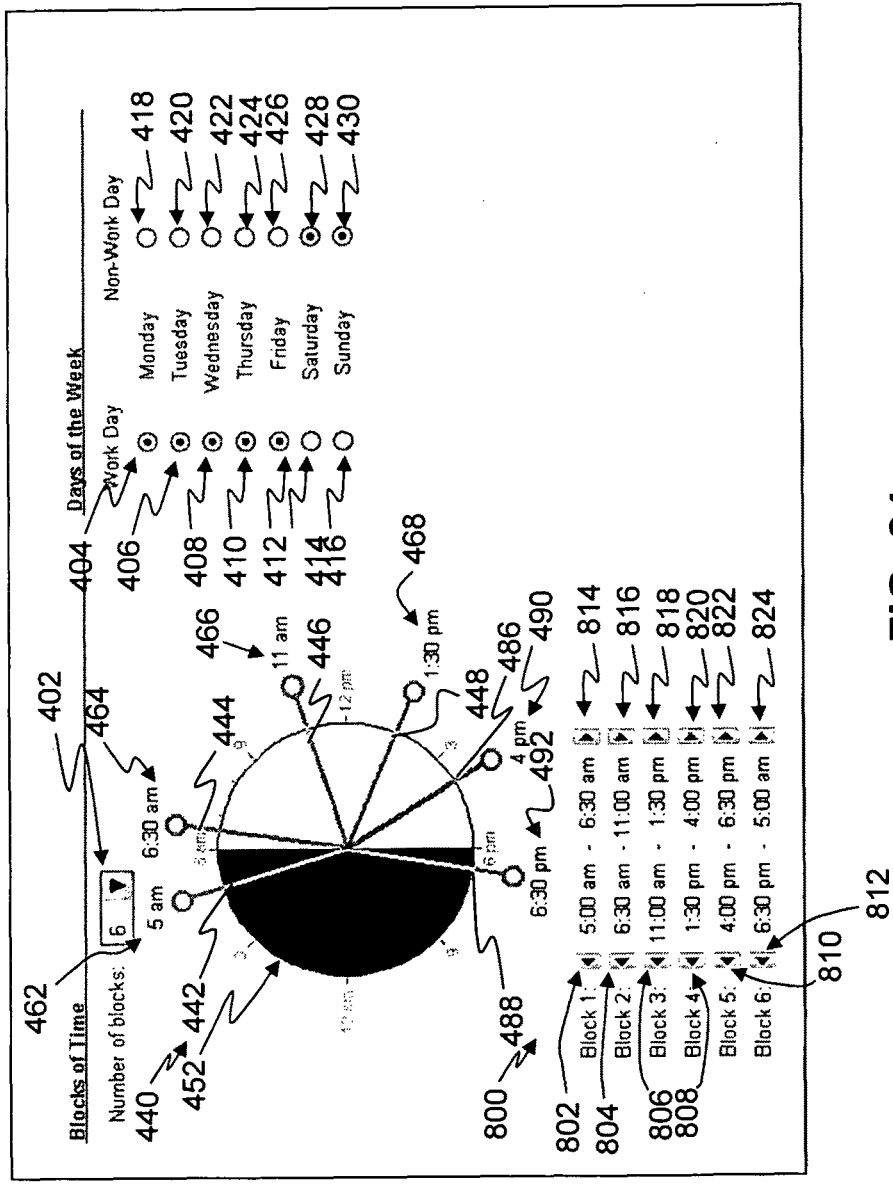
FIG. 24 is yet a further exemplary input device for setting time blocks.

Referring to FIG. 24, a selection input 800 is shown. Selection input 800 is shown in combination with selection input 440. This provides a user with two ways to adjust the time for a given time block. Selection input 800 includes a plurality of decrement inputs 802, 804, 806, 808, 810, and 812 corresponding to respective time blocks 380, 382, 384, 386, 388, and 390 and a plurality of increment inputs 814, 816, 818, 820, 822, and 824 corresponding to respective time blocks 380, 382, 384, 386, 388, and 390. Each of decrement inputs and increment inputs move the endpoint of the respective time block. As such, if you wanted to adjust the beginning of time block 384 (the third time block), you would use decrement input 804 or increment input 816 of the second time block.

The number of time blocks and time periods corresponding to each may be used by a caregiver and/or patient to better analyze the blood glucose values and other physiological information 110 of the patient. One way in which this is done is through reports and/or graphs of the collected physiological information 110. Exemplary graphs are shown in FIGS. 14-18.

Figure 14:
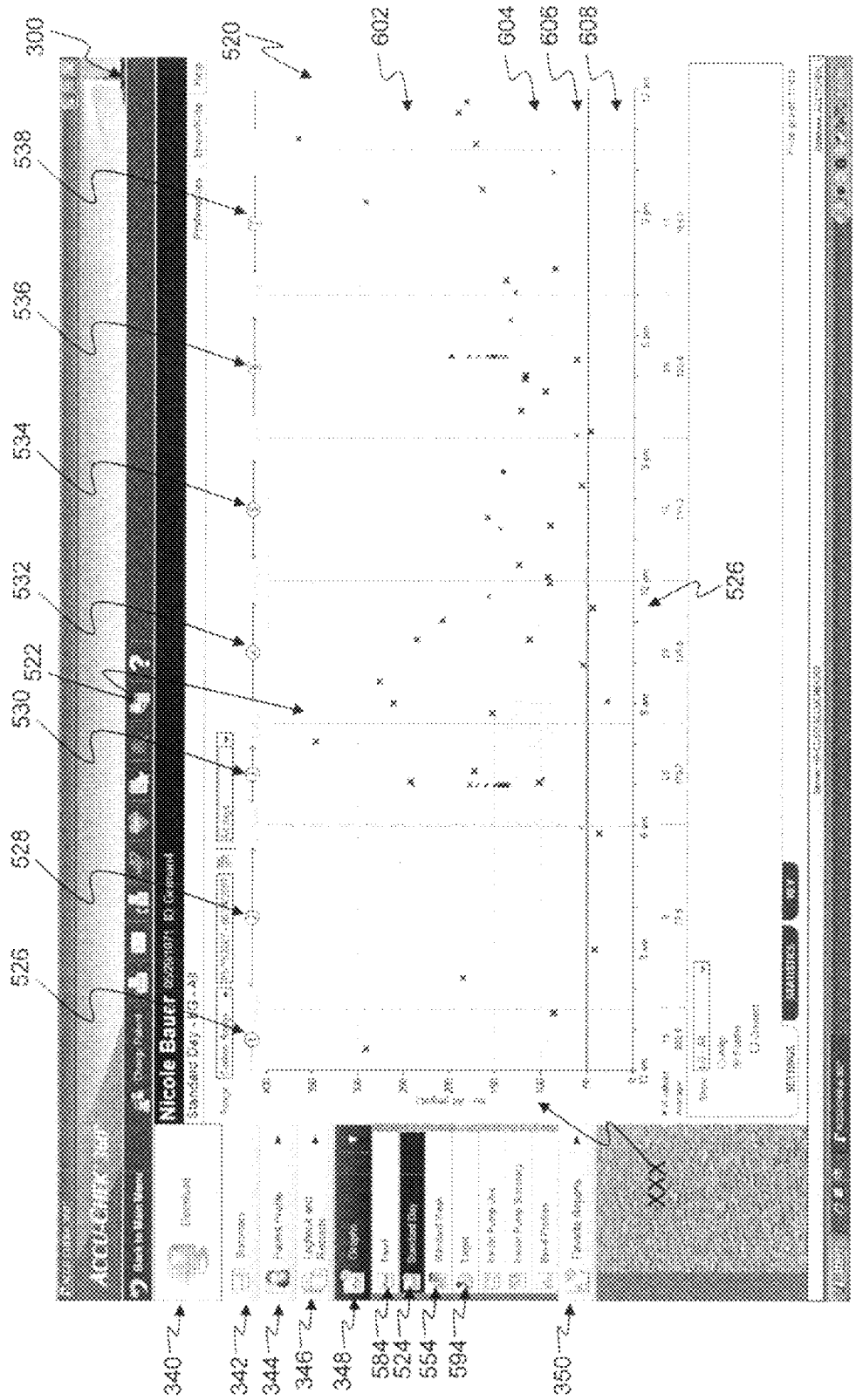
FIG. 14 is an exemplary standard day graph screen of a user interface of a healthcare management software system.

Referring to FIG. 14, a screen 520 is shown. Screen 520 includes a standard day chart or graph 522 selected through the selection of the graphs selection input 348 (see FIG. 9) and a standard day graph selection input 524. As shown in the standard day graph 522, the 24-hour times for a given day are shown along the X axis 526 of graph 522. In the standard day graph 522, blood glucose values (illustrated as "x" marks) are grouped by the time block of the day. Along the top portion of graph 522, each of the seven selected time blocks 380, 382, 384, 386, 388, 390, and 392 are indicated by a corresponding textual label 526, 528, 530, 532, 534, 536, and 538. In relation to the time blocks defined by the user, the user can better quantify the effect of various events on their blood glucose values.

Figure 15:
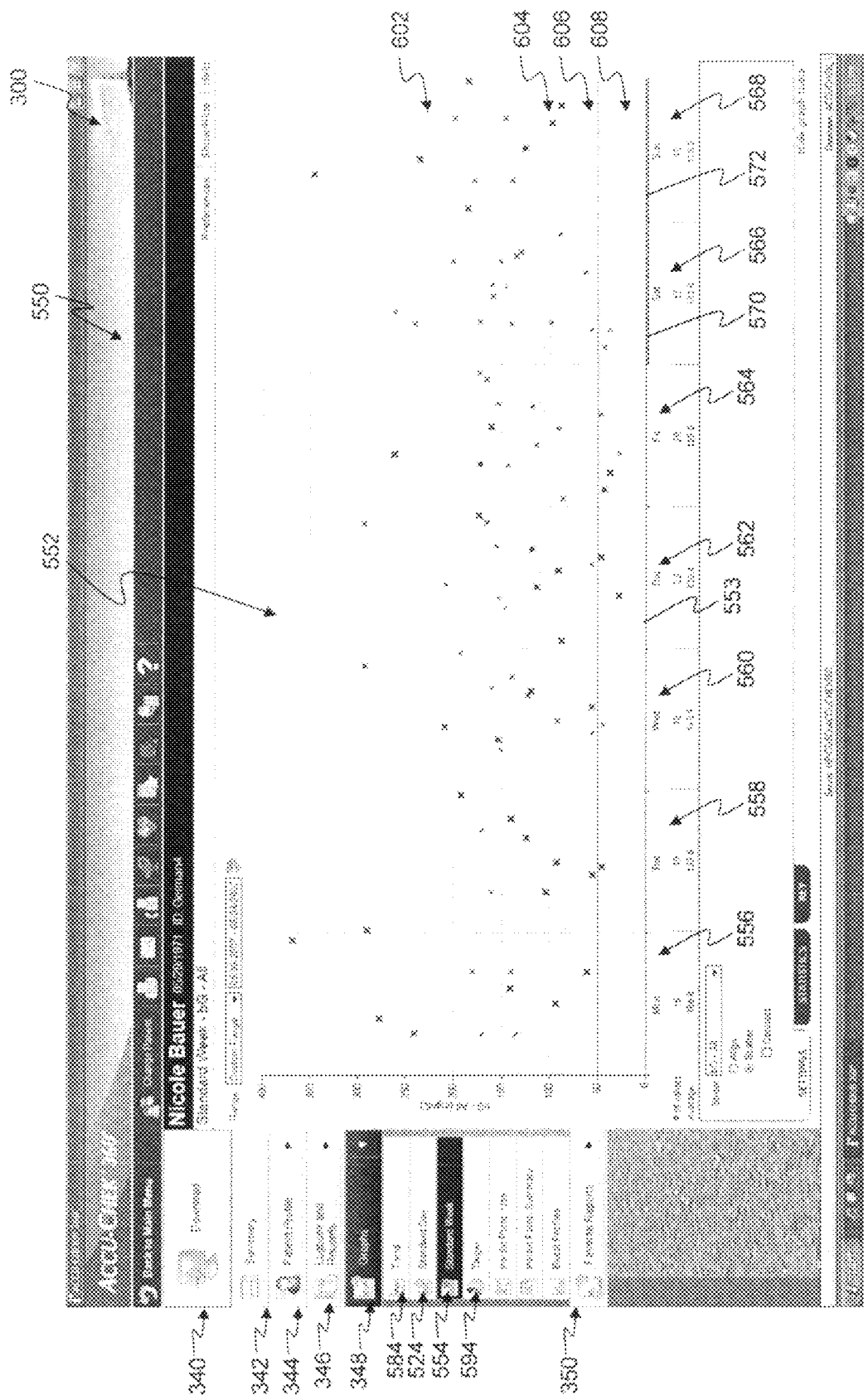
FIG. 15 is an exemplary standard week graph screen of a user interface of a healthcare management software system.

Referring to FIG. 15, a screen 550 is shown. Screen 550 shows a standard week graph 552, which is displayed in response to the selection of graphs selection input 348 and the standard week selection input 554. In the standard week graph 552, blood glucose values (illustrated as "x" marks) are grouped by the day of the week. Each day of the week is represented along the X axis 553 of the graph as textual labels 556 through 568. Further, the non-work days, illustratively Saturday and Sunday, are represented by a visual indicator 570 and 572, respectively. The standard week graph 552 permits the user to see if there are fluctuations between days of a first classification, such as work days, and days of a second classification, such as non-work days.

Figure 16:
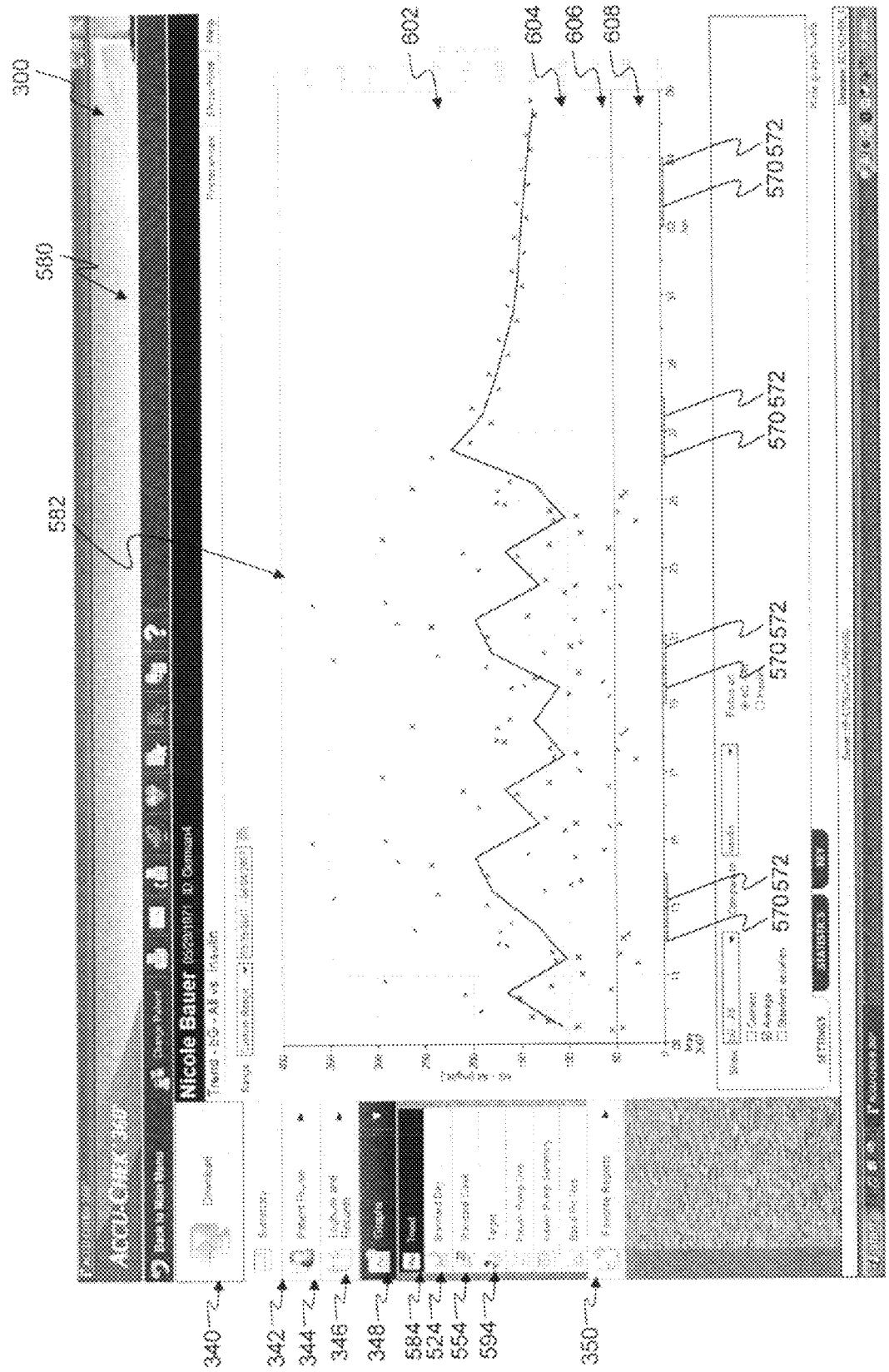
FIG. 16 is an exemplary trend graph screen of a user interface of a healthcare management software system.

Referring to FIG. 16, a screen 580 is shown. Screen 580 correspond to a trend graph 582. Trend graph 582 is displayed in response to the selection of the graphs selection input 348 and the trend selection input 584. The trend graph 582 shows the blood glucose values (illustrated as "x" marks) over a period of time, such as multiple weeks. Further, the non-work days, illustratively Saturday and Sunday, are represented by visual indicators 570 and 572, respectively.

Figure 17:
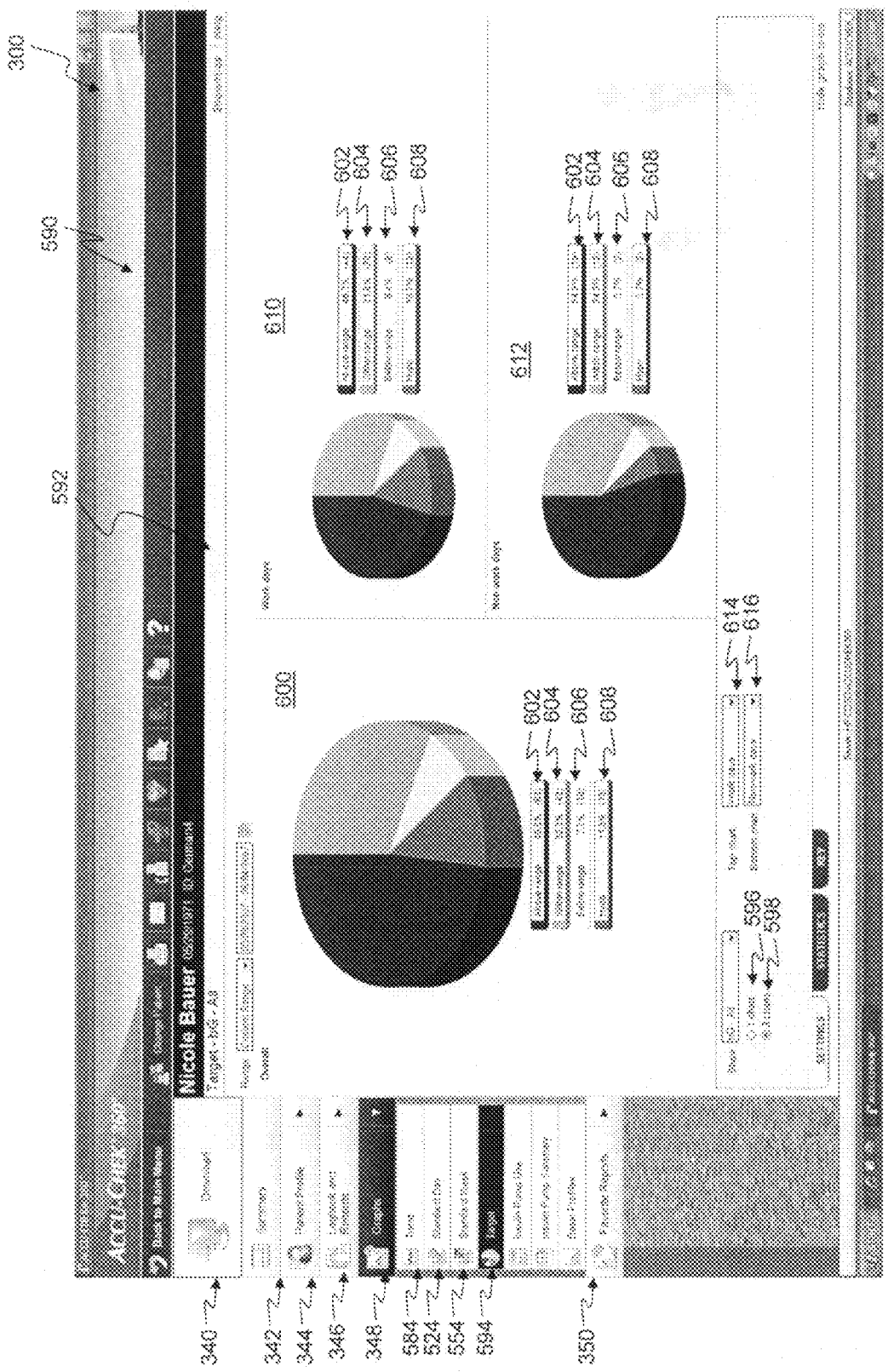
FIG. 17 is an exemplary target graph screen of a user interface of a healthcare management software system including a comparison of a first type of day and a second type of day.

Referring to FIG. 17, a screen 590 is shown, which includes one or more target graphs 592, which are displayed in response to the graphs selection input 348 and the target selection input 594. A user may select to see a single chart with selection input 596 or three charts with the selection input 598. Illustratively, three charts are shown. A first chart 600 shows the overall blood glucose values breakdown. Blood glucose values are broken down into four categories above the target blood glucose value 602, within a target blood glucose value range 604, below the target blood glucose value range 606, and hypoglycemic values as represented by 608. These four categories are also illustrated in the graphs in FIGS. 14-16. The overall blood glucose values may be broken down by various criteria and provided in charts 610 and 612. The criteria for charts 610 and 612 are selected through selection input 614 and 616, respectively.

As shown in FIG. 17, the criteria for the top chart 610 is a first classification of the days of the week, work days, and the criteria for the bottom graph 612 is a second classification of the days of the weeks, non-work days. Each graph 610 and 612 also includes the four changes of blood glucose values 602, 604, 606, and 608.

Figure 18:
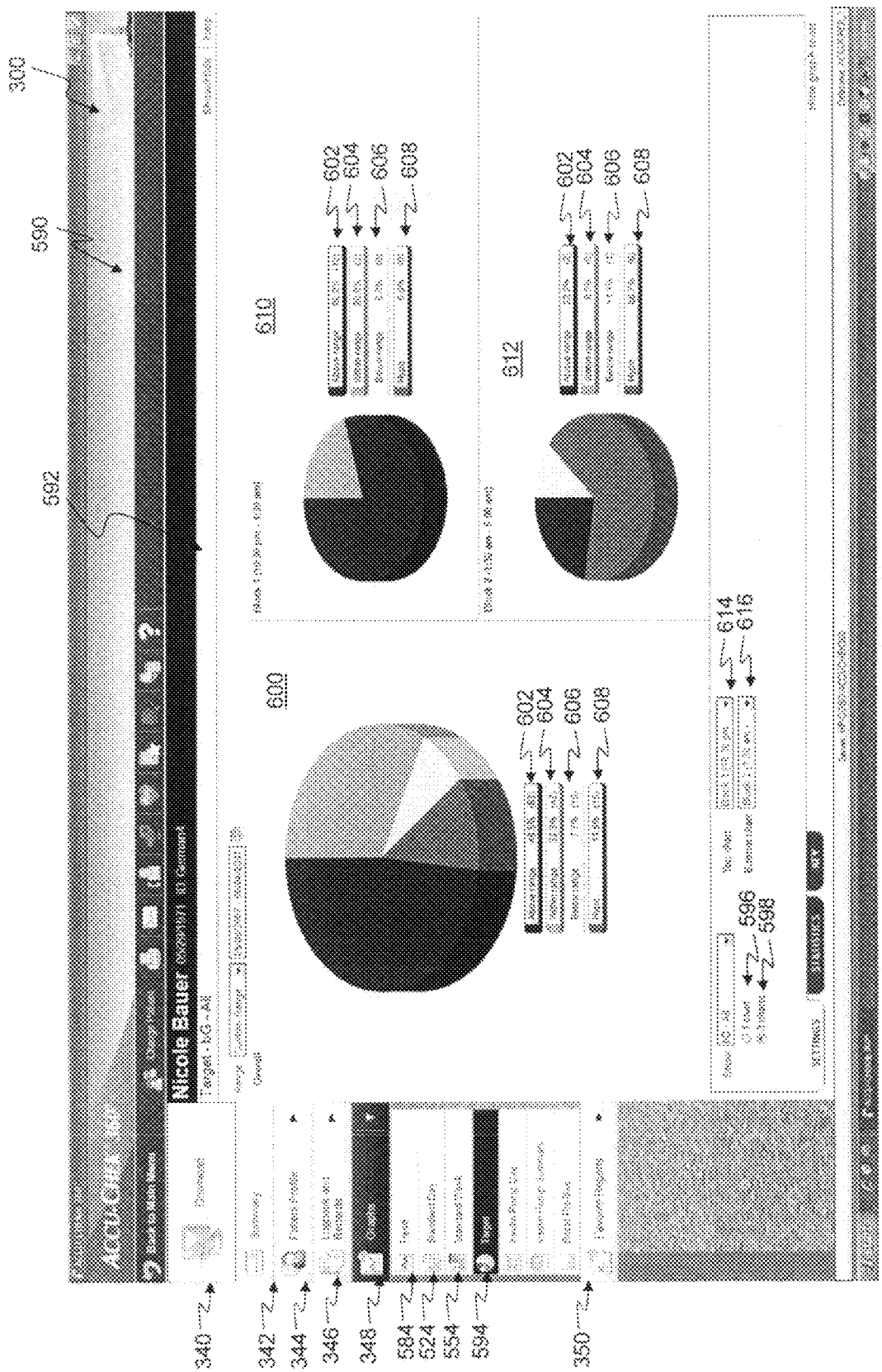
FIG. 18 is an exemplary target graph screen of a user interface of a healthcare management software system including a comparison of a first time block and a second time block.

Referring to FIG. 18, another target graph 592 is shown. In FIG. 18, the criteria for selection input 614 has changed from work days to the first time block of time, and the criteria for selection input 616 has changed from non-work days to the second time block of time. This permits the user to be able to see the breakdown of blood glucose values within a given time block.

The concept of repeating time periods and time blocks have been used herein throughout. The selection inputs and methods discussed herein may also be used for sub-dividing any type of periodic parameter, repeating time periods being one example thereof. Also, the dragging of spokes may be extended to the setting of an electronic clock by simply dragging the hands of the clock to set the time.

In one embodiment, the setting of the time blocks is used as a method of classifying data received, such as blood glucose values, insulin delivery values, or other measured physiological parameter values. In one embodiment, the setting of time blocks is used to program events. An exemplary event is the provision of insulin with an insulin pump. In one example, one or more time blocks may provide a generally constant rate of insulin during the time block, although each time block may provide a different rate of insulin or no insulin at all. In one example, a bolus amount of insulin may be at the beginning of a respective time block or at some time within a respective time block.

Although the invention has been described in detail with reference to certain preferred embodiments, variations and modifications exist within the spirit and scope of the invention as described and defined in the following claims.

The invention claimed is:

1. A method of adjusting durations of time blocks used in a healthcare management software system, the method including the steps of:
    receiving, by the a computing device, a plurality of blood glucose measures for a patient;
    receiving, by the computing device, one input to identify a plurality of time blocks for a repeating time period;
    receiving, by the computing device, one or more duration selections related to a duration for at least one of the time blocks, each of the time blocks having a start time and an end time, and the end time of each of the time blocks generally defining the start time of a subsequent time block;
    displaying, by the computing device, the repeating time period on a graphical display of the computing device, where the repeating time period is represented by a circle with time block dividers emanating from a center of the circle and extending at least to a circumference of the circle, thereby dividing the circle into the plurality of time blocks, such that each time period between two adjacent time block dividers correlate to the duration selected for the corresponding time block;
    adjusting, by the computing device, duration of a given time block in accordance with positions of the time block dividers, where the adjustment occurs in response to user input on the graphical display that changes position of at least one time block divider;
    analyzing, by the computing device, the plurality of blood glucose measures in accordance with the adjusted time blocks, where the steps of displaying, adjusting and analyzing are implemented by computer executable instructions executed by a computer processor of the computing device; and
    provisioning, by an insulin pump, insulin according to the adjusted time blocks.

2. The method of claim 1, wherein the number of time blocks is at least two and up to forty-eight.

3. The method of claim 1, wherein the one or more duration selections are based on a selected position of one or more time block dividers provided on a user interface of a computing device.

4. The method of claim 3, wherein the time block dividers are positioned relative to a clock representation of the repeating time period, the time block dividers being spokes emanating from a center of the clock representation of the repeating time period.

5. The method of claim 4, wherein a first time block divider separates a first time block and a second time block, a duration of the first time block and a duration of the second time block both being altered by rotating the first time block divider relative to the clock representation of the repeating time period.

6. The method of claim 5, further including providing for each time block a textual label.

7. The method of claim 6, further including receiving, by the computing device, a label text for at least one textual label, the label text being user-specified.

8. The method of claim 6, wherein the textual label for a respective time block is provided between the two time block dividers bounding the respective time block.

9. The method of claim 6, wherein the textual label for a respective time block is provided as a part of one of the time block dividers bounding the respective time block.

10. The method of 1, further including the steps of:
    receiving, the plurality of blood glucose measures with corresponding test times;
    graphically presenting the plurality of blood glucose measures in relation to the time blocks.

11. The method of claim 10, wherein the step of graphically presenting the plurality of blood glucose measures based on the time block including the corresponding test time includes the steps of:
    graphically representing the plurality of time blocks;
    graphically representing the plurality of blood glucose measures; and
    graphically representing a plurality of classifications for the plurality of blood glucose measures.

12. The method of claim 11, wherein the plurality of classifications include a target classification.

13. The method of claim 10, wherein the plurality of blood glucose values and corresponding test times are provided by a blood glucose meter.

14. The method of claim 10, wherein the plurality of blood glucose values and corresponding test times are provided by an infusion pump.

15. The method of claim 1, further including the steps of:
    receiving, using the software system, a first type selection for a first instance of the repeating time period; and
    receiving, using the software system, a second type selection for a second instance of the repeating time period.

16. A method for managing time blocks in a healthcare management software system, the method including the steps of:
    receiving, by a computing device, a plurality of physiological parameter values for a patient;
    receiving, by the computing device, one input to identify a plurality of time blocks for a repeating time period;
    receiving, by the computing device, one or more duration selections related to a duration for at least one of the time blocks, each of the time blocks having a start time and an end time;
    displaying, by the computing device, the repeating time period on a graphical display of the computing device, where the repeating time period is represented by a circle with selection spokes emanating from a center of the circle and extending at least to a circumference of the circle, thereby dividing the circle into the plurality of time blocks, such that each time period between two adjacent time block dividers correlate to the duration selected for the corresponding time block;

adjusting, by the computing device, duration of a given time block in accordance with positions of the selection spokes, where the adjustment occurs in response to user input on the graphical display that changes position of at least one selection spoke; and grouping, by the computing device, the plurality of physiological parameter values by the adjusted time blocks in response to the adjusted time blocks; and graphically presenting, by the computing device, the plurality of physiological parameter values in relation to the adjusted time blocks and in response to the adjusted time blocks, where the steps of displaying, adjusting, grouping and presenting are implemented by computer executable instructions executed by a computer processor of the computing device.

17. The method of claim 16, further including the steps of:

receiving, by the computing device, a plurality of physiological parameter values and corresponding test times; and graphically presenting the plurality of physiological parameter values based on the time block including the corresponding test time.

18. The method of claim 17, wherein the physiological parameter values are insulin delivery values, the plurality of insulin delivery values and corresponding test times are provided by an infusion pump.

19. The method of claim 17, wherein the step of graphically presenting the plurality of physiological parameter values based on the time block including the corresponding test time includes the steps of:

graphically representing the plurality of time blocks;

graphically representing the plurality of physiological parameter values; and graphically representing a plurality of classifications for the plurality of physiological parameter values, including a target classification.

20. The method of claim 17, wherein the physiological parameter values are blood glucose values, the plurality of blood glucose values and corresponding test times are provided by a blood glucose meter.

21. The method of claim 17, wherein the physiological parameter values are blood glucose values, the plurality of blood glucose values and corresponding test times are provided by an infusion pump.

22. A method for managing time blocks associated with a patient, the method including the steps of:

receiving, by a computing device, physiological information from the patient;

displaying, by the computing device, a plurality of positionable time block dividers and a clock representation of a repeating time period on a graphical display of the computing device, the plurality of positionable time block dividers being spokes emanating from a center of the clock representation of the repeating time period and extending past a circumference of the clock representation, and each time block divider being configured for adjustment relative to other time block dividers;

receiving, by the computing device, a change in position of a first time block divider made by moving the position of the first time block divider in the clock representation;

determining, by a computing device, a duration of a first time block and a duration of a second time block based on the received position of the first time block divider, the first time block divider defining an end point for the first time block and a start point for the second time block;

analyzing, by the computing device, the physiological information in accordance with the adjusted duration of the first and second time blocks, where the steps of displaying, determining and analyzing are implemented by computer executable instructions executed by a computer processor of the computing device; and provisioning insulin, by an insulin pump, according the adjusted duration of the first time block and provisioning insulin, by the insulin pump, according the adjusted duration of the second time block.

23. The method of claim 22, wherein the duration of the first time block and the duration of the second time block both being altered by rotating the first time block divider relative to the clock representation of the repeating time period.

24. The method of claim 22, further including providing for each time block a textual label on the graphical display adjacent to the corresponding time block.

25. The method of claim 24, further including receiving, by the computing device, a label text for at least one textual label, the label text being user-specified.

26. The method of claim 24, wherein the textual label for a respective time block is provided between the two time block dividers bounding the respective time block.

27. The method of claim 24, wherein the textual label for a respective time block is provided as a part of one of the time block dividers bounding the respective time block.

* * * * *